(12) United States Patent
Raab et al.

(10) Patent No.: US 9,623,185 B2
(45) Date of Patent: Apr. 18, 2017

(54) ASSEMBLY FOR A DRUG DELIVERY DEVICE AND DRUG DELIVERY DEVICE

(75) Inventors: Steffen Raab, Frankfurt am Main (DE); Mark Philip Horlock, Timperley (GB); Stephen David Butler, Essington (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1112 days.

(21) Appl. No.: 13/701,969

(22) PCT Filed: Jun. 9, 2011

(86) PCT No.: PCT/EP2011/059566
§ 371 (c)(1),
(2), (4) Date: Apr. 10, 2013

(87) PCT Pub. No.: WO2011/154482
PCT Pub. Date: Dec. 15, 2011

(65) Prior Publication Data
US 2013/0211342 A1     Aug. 15, 2013

(30) Foreign Application Priority Data

Jun. 11, 2010   (EP) .................................... 10165639

(51) Int. Cl.
*A61M 5/315*    (2006.01)
*A61M 5/24*     (2006.01)

(52) U.S. Cl.
CPC .......... *A61M 5/31511* (2013.01); *A61M 5/24* (2013.01); *A61M 5/3155* (2013.01);
(Continued)

(58) Field of Classification Search
CPC .......... A61M 5/31585; A61M 5/31551; A61M 5/31553; A61M 5/31555; A61M 5/31543;
(Continued)

(56) References Cited

U.S. PATENT DOCUMENTS

| 5,725,508 A | 3/1998 | Chanoch et al. |
| 5,827,232 A | 10/1998 | Chanoch et al. |

(Continued)

FOREIGN PATENT DOCUMENTS

| JP | H08-730 B2 | 1/1996 |
| JP | H7-500039 | 4/2000 |

(Continued)

OTHER PUBLICATIONS

Form PCT/IB/326, Notification Concerning Transmittal International Preliminary Report on Patentability.
(Continued)

*Primary Examiner* — Laura Bouchelle
*Assistant Examiner* — Anh Bui
(74) *Attorney, Agent, or Firm* — McDonnell Boehnen Hulbert & Berghoff LLP

(57) ABSTRACT

An assembly for a drug delivery device is provided, comprising a housing, a rotation member adapted and arranged to be rotated in a first and in a second rotational direction with respect to the housing in an operational mode of the assembly, a drive member which is configured to mechanically cooperate with the rotation member such that the drive member follows rotation of the rotation member when the rotation member is rotated in the second rotational direction and such that the rotation member rotates with respect to the drive member when the rotation member is rotated in the first rotational direction, and a piston rod. The assembly further comprises at least one biasing member which is adapted and arranged to provide a force tending to bring the rotation member and the drive member out of mechanical cooperation in the operational mode. The assembly is switchable from the operational mode into a reset mode. For switching from the operational mode into the reset mode, the biasing member is configured to drive a relative axial
(Continued)

movement between the drive member and the rotation member such that the rotation member and the drive member are brought out of mechanical cooperation. Furthermore, a drug delivery device is provided.

16 Claims, 11 Drawing Sheets

(52) U.S. Cl.
CPC ...... *A61M 5/3158* (2013.01); *A61M 5/31551* (2013.01); *A61M 5/31553* (2013.01); *A61M 5/31555* (2013.01); *A61M 5/31583* (2013.01); *A61M 5/31585* (2013.01); *A61M 5/31543* (2013.01)

(58) Field of Classification Search
CPC ............ A61M 5/3158; A61M 5/31583; A61M 5/3155
See application file for complete search history.

(56) References Cited

U.S. PATENT DOCUMENTS

| | | | |
|---|---|---|---|
| 8,512,296 | B2 | 8/2013 | Gabriel et al. |
| 9,057,369 | B2 | 6/2015 | Kohlbrenner et al. |
| 2002/0111587 | A1 | 8/2002 | Hommann et al. |
| 2006/0153693 | A1* | 7/2006 | Fiechter ............ A61M 5/31553 417/63 |
| 2007/0123829 | A1 | 5/2007 | Atterbury et al. |
| 2009/0275914 | A1 | 11/2009 | Harms et al. |

FOREIGN PATENT DOCUMENTS

| | | |
|---|---|---|
| JP | 2006-187628 A | 7/2006 |
| WO | 93/07922 | 4/1993 |
| WO | 9307922 A1 | 4/1993 |
| WO | 2004093940 A2 | 11/2004 |
| WO | 2006/058061 | 6/2006 |
| WO | 2008145171 A1 | 12/2008 |

OTHER PUBLICATIONS

International Search Report for Int. App. No. PCT/EP2011/059566, completed Dec. 5, 2011.
English Translation of Notice of Reason for Rejection issued in Japanese Patent Application No. 2013-513688 dated Nov. 4, 2015.
English translation of Decision of Rejection issued in Japanese Patent application No. 2013-513688 dated Jul. 5, 2016.

\* cited by examiner

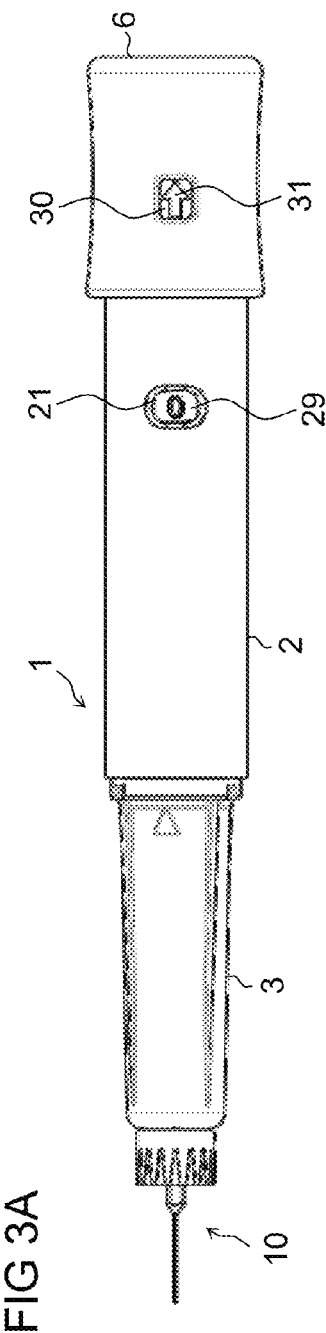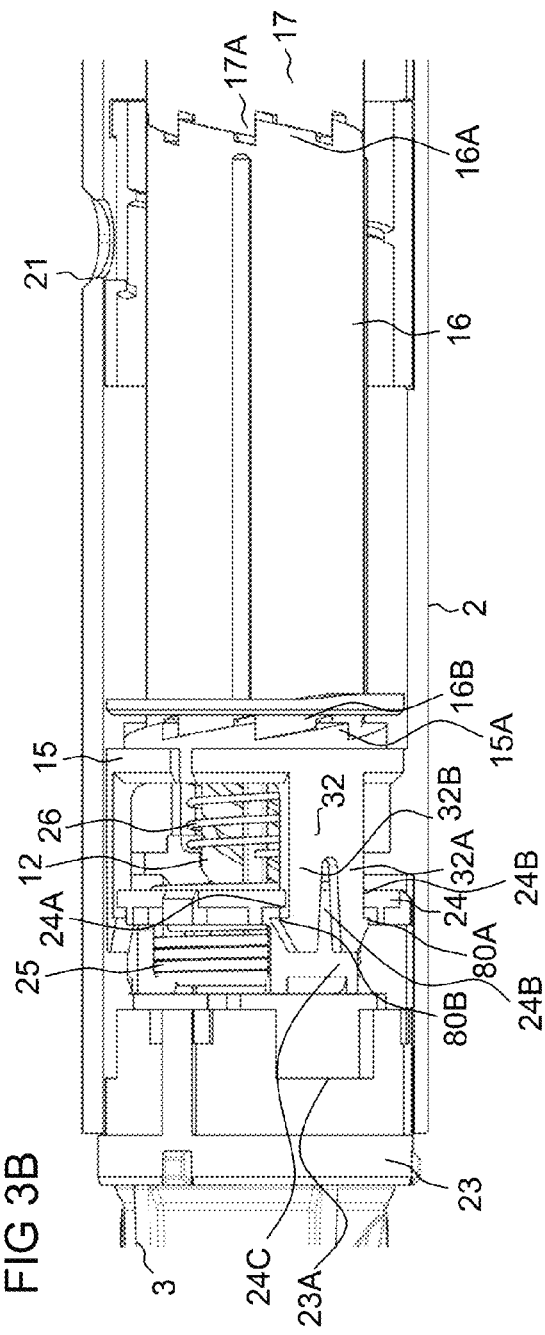
FIG 3A
FIG 3B

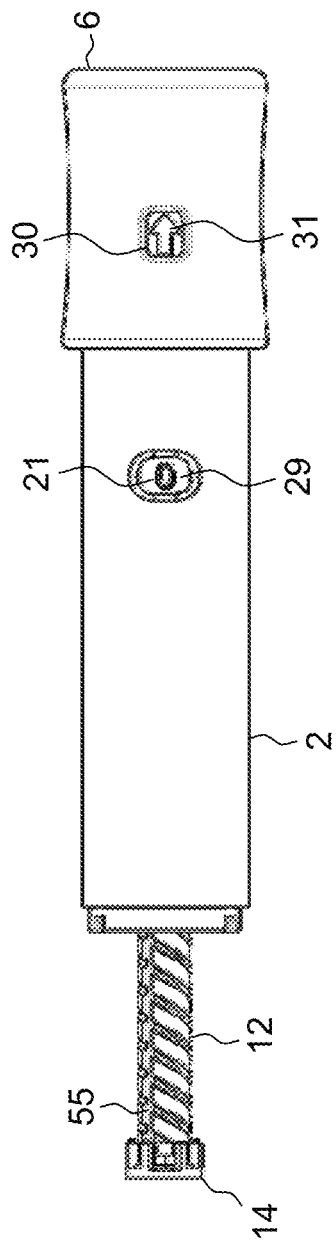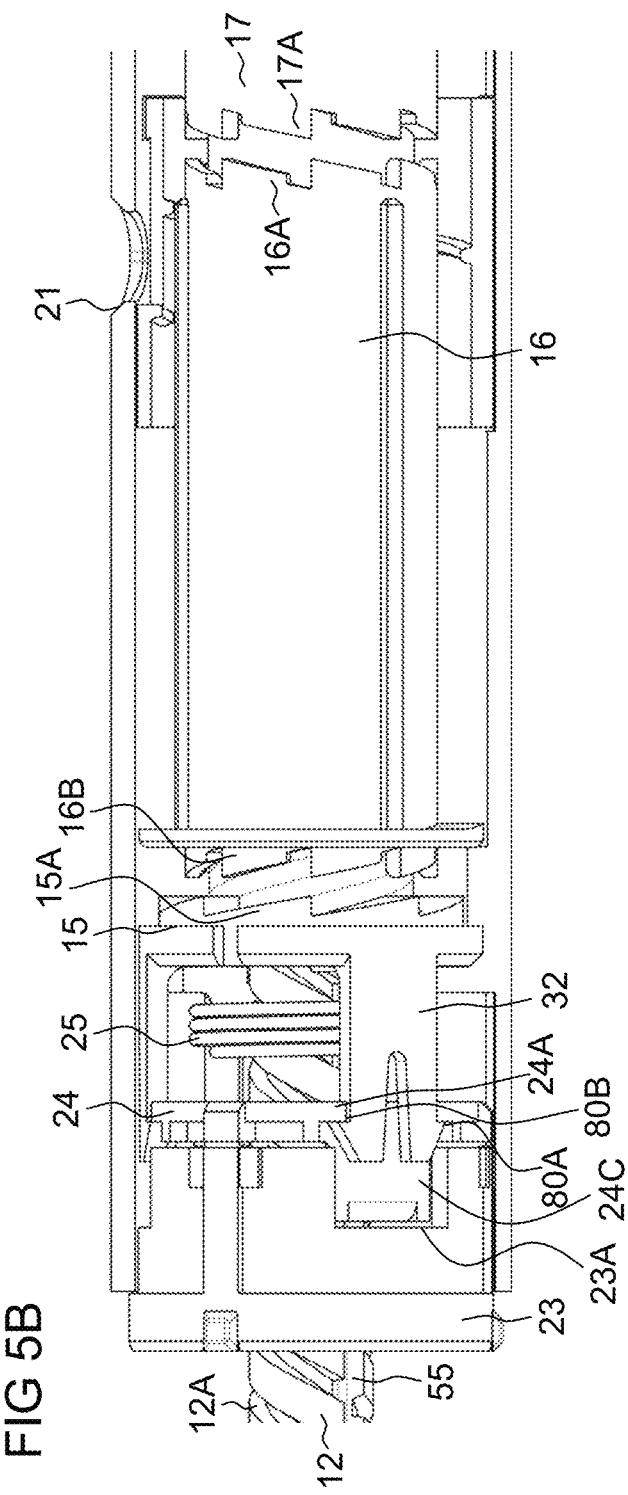
FIG 5A
FIG 5B

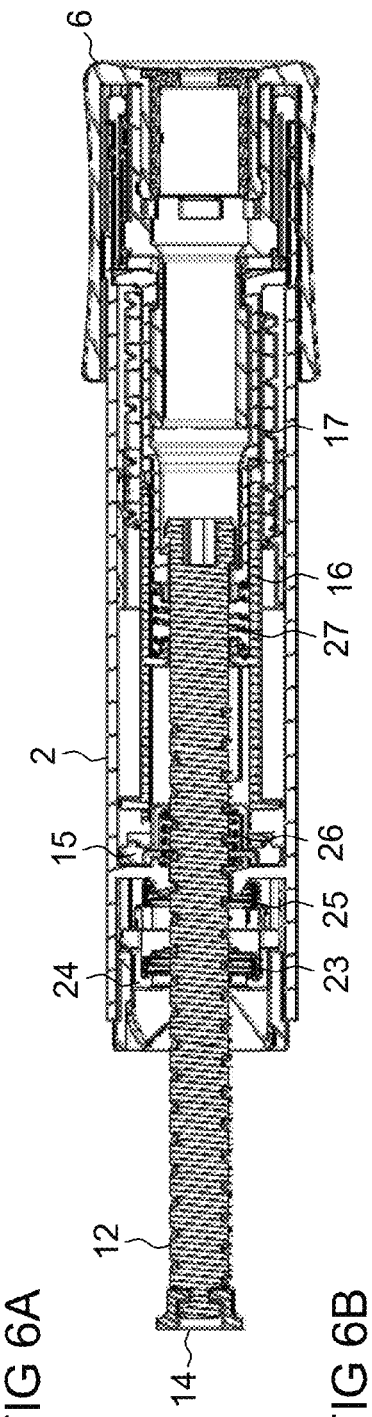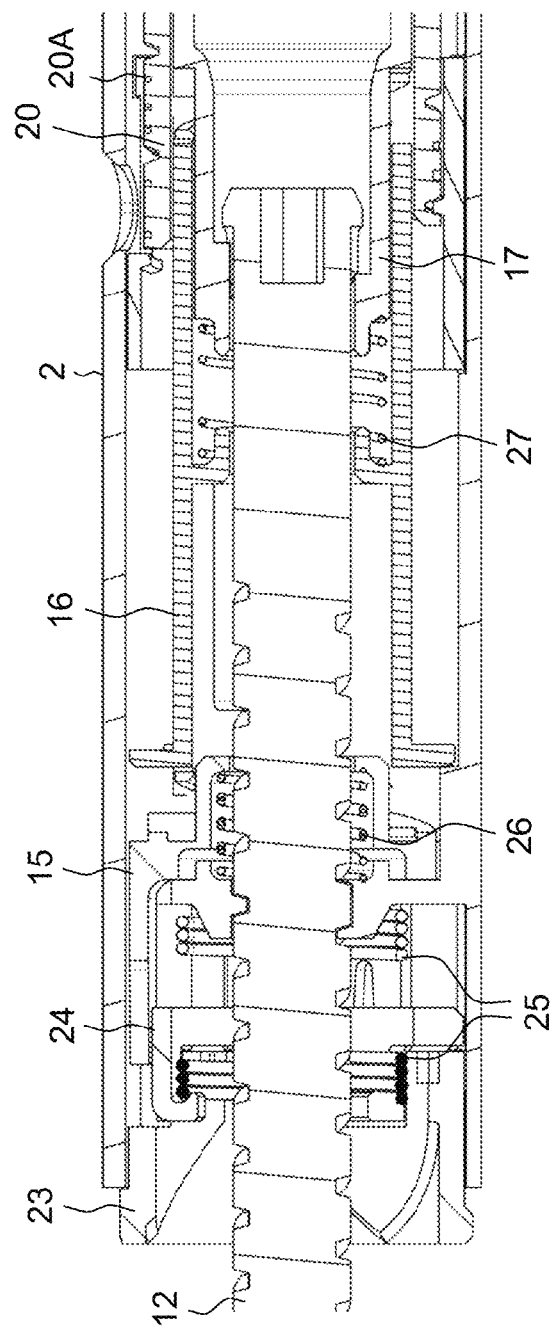

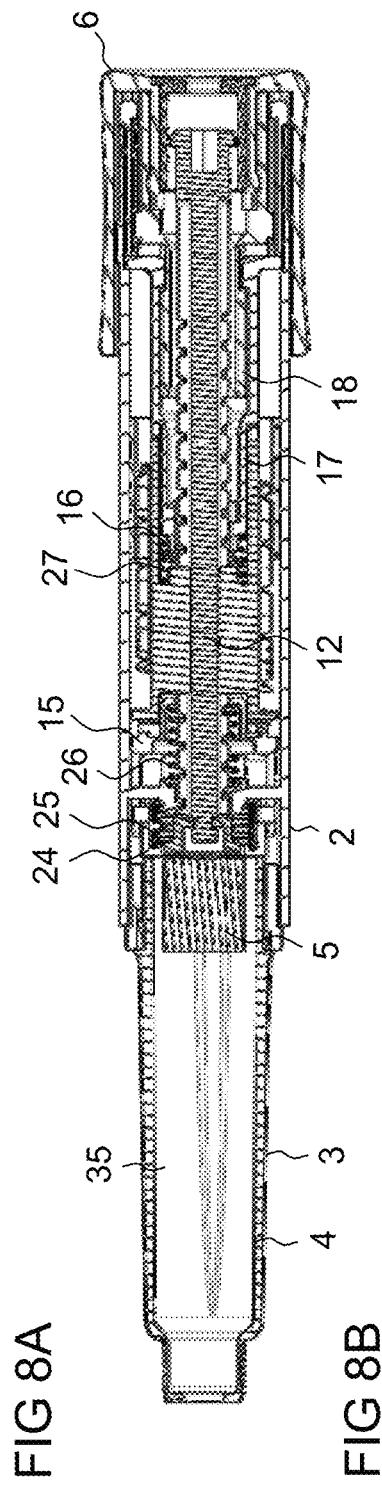
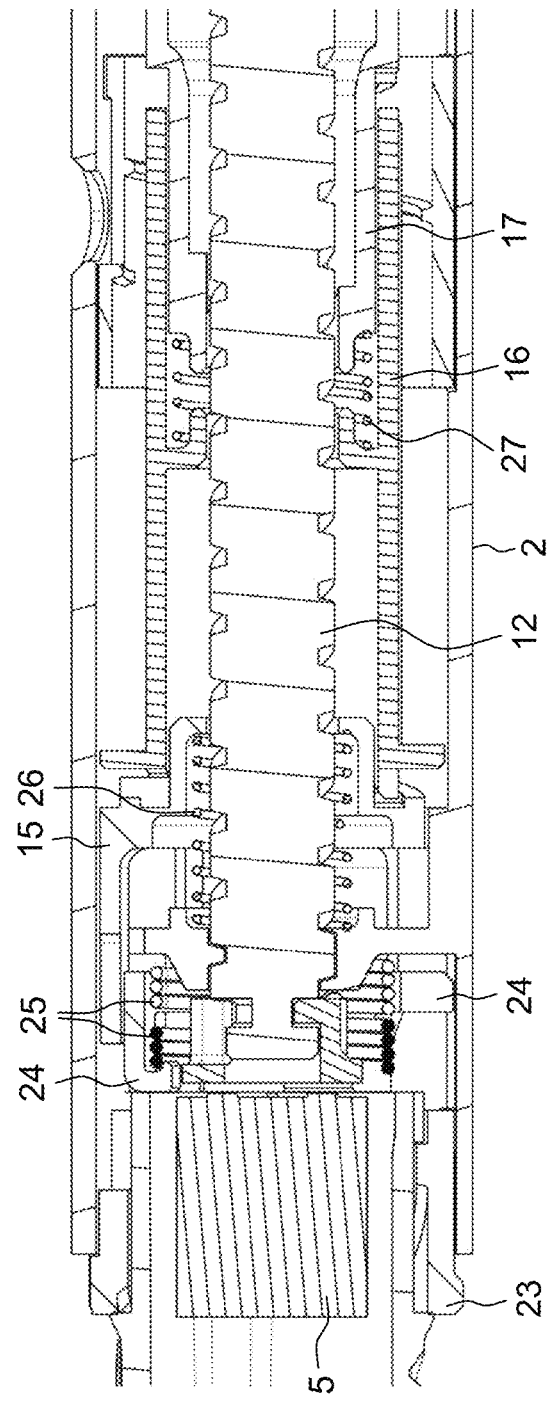
FIG 8A
FIG 8B

ASSEMBLY FOR A DRUG DELIVERY DEVICE AND DRUG DELIVERY DEVICE

CROSS REFERENCE TO RELATED APPLICATIONS

The present application is a U.S. National Phase application pursuant to 35 U.S.C. §371 of International Application No. PCT/EP2011/059566 filed Jun. 9, 2011, which claims priority to European Patent Application No. 10165639.5 filed on Jun. 11, 2010. The entire disclosure contents of these applications are herewith incorporated by reference into the present application.

FIELD OF INVENTION

This disclosure relates to an assembly for a drug delivery device and a drug delivery device incorporating such an assembly.

BACKGROUND

A drug delivery device may comprise a cartridge containing a drug. For expelling a dose of the drug from the cartridge, a bung within the cartridge may be displaced by a piston rod of a drive mechanism of the device.

A drug delivery device is described in US 2007/0123829 A1, for example.

SUMMARY

It is an object of the present disclosure to facilitate provision of a novel, preferably an improved, drug delivery device.

This object may be achieved by the subject matter of the independent claim. Further features and advantageous embodiments are the subject matter of the dependent claims.

According to one aspect, an assembly for a drug delivery device is provided. The assembly may comprise a housing. The housing may have a distal end and a proximal end. The assembly may comprise a rotation member. The rotation member is expediently adapted and arranged to be rotated in a first rotational direction with respect to the housing in an operational mode, e.g. a dose setting and/or a dose delivery mode, of the assembly. The rotation member may be adapted and arranged to be rotated in a second rotational direction with respect to the housing in the operational mode of the assembly. The assembly may comprise a drive member. The drive member may be configured to mechanically cooperate, in particular to engage, with the rotation member. In the operational mode, the drive member may be in direct mechanical contact, preferably permanent direct mechanical contact, with the rotation member. Preferably, the drive member mechanically cooperates with the rotation member such that the drive member follows rotation of the rotation member when the rotation member is rotated in the second rotational direction. The drive member may mechanically cooperate with the rotation member such that the rotation member rotates with respect to the drive member when the rotation member is rotated in the first rotational direction. The assembly may comprise a piston rod. The piston rod may mechanically cooperate with the drive member. The piston rod may be adapted and arranged to be driven in the distal direction with respect to the housing when the drive member is rotated in the second rotational direction. The assembly may comprise at least one biasing member. The biasing member is preferably adapted and arranged to provide a force tending to bring the rotation member and the drive member out of mechanical cooperation in the operational mode. The assembly may be switchable from the operational mode into a reset mode for resetting the device. For switching into the reset mode, the drive member and the rotation member may be adapted and arranged to be moved relatively to each other, preferably to bring the drive member and the rotation member out of mechanical cooperation. In the reset mode, direct mechanical contact between the drive member and the rotation member may be prevented. Preferably, for switching from the operational mode into the reset mode, the biasing member is configured to drive a relative axial movement between the drive member and the rotation member such that the rotation member and the drive member are brought out of mechanical cooperation.

The biasing member facilitates an automatical switching of the assembly from the operational mode into the reset mode. In the reset mode, mechanical cooperation of the drive member and the rotation member may be prevented by means of the biasing member. In the reset mode, the drive member may be rotatable in the first rotational direction with respect to the rotation member. In the operational mode, this rotation may be prevented or at least impeded. Accordingly, in the reset mode, the piston rod may be moveable in the proximal direction with respect to the housing.

A further aspect relates to a drug delivery device. The drug delivery device expediently comprises the assembly described above. The device may comprise a cartridge. The cartridge may hold one dose, preferably a plurality of doses, of a drug. The drug delivery device may be a pen-type device. The device may be a fixed dose device, in particular a device for dispensing doses which may not be varied by a user. The device may be a pen-type fixed dose device.

The drug delivery device may be an injection device, e.g. a pen-type injector. Preferably, the device is a reusable device. After having dispensed the plurality of doses of the drug held in the cartridge, the cartridge may be removed. Afterwards, the device may be reset, in particular the piston rod may be moved proximally back into a proximal starting position it occupied before the first dose was dispensed. Finally, a replacement cartridge holding at least one dose, preferably a plurality of doses, of a drug may be introduced into the device.

According to an embodiment, the assembly comprises a stop member. The drive member and the stop member may be coupled to one another by a uni-directional clutch mechanism, preferably a friction clutch mechanism, in the operational mode. In the operational mode, the drive member may be in direct mechanical contact, preferably permanent direct mechanical contact, with the stop member. In the operational mode, the drive member and the stop member may be, preferably permanently, coupled such that rotation of the drive member in the first rotational direction with respect to the stop member is prevented. In the operational mode, the drive member and the stop member may be, preferably permanently, coupled such that rotational movement of the drive member in the second rotational direction with respect to the stop member is permitted.

For switching from the operational mode into the reset mode, the drive member and the stop member may be brought out of mechanical cooperation. Accordingly, in the reset mode, the drive member and the stop member may be decoupled such that rotational movement of the drive member in the first rotational direction with respect to the stop member is permitted. In particular, in the reset mode, direct mechanical contact between the drive member and the stop member may be prevented. Accordingly, in the reset mode, the piston rod may be moveable in the proximal direction with respect to the housing.

According to an embodiment, the drive member and the piston rod are rotationally locked with, preferably splined to, each other.

The drive member may be coupled to the piston rod so as to convert its rotational movement in the second rotational direction at least partially into rotational movement of the piston rod with respect to the housing, in particular rotational movement in the same direction and/or by the same angle, e.g. when delivering a dose. Rotation in the first direction may cause undesirable proximal movement of the piston rod. Accordingly, the risk of the piston rod being moved in the proximal direction during dose setting can be reduced by preventing rotational movement of the drive member in the first rotational direction in the operational mode. Unintentional proximal movement of the piston rod may result in decreased dose accuracy. Consequently, dose accuracy may be improved by avoiding proximal movement of the piston rod.

In the reset mode, rotational movement of the drive member in the first rotational direction may be allowed due to the drive member being disengaged from the stop member and/or the rotation member. Accordingly, proximal movement of the piston rod, in particular movement of the piston rod towards a proximal starting position, for resetting the device may be enabled in the reset mode.

According to an embodiment, the stop member is rotationally locked to the housing. The stop member may be rotationally locked to the housing in the reset mode and/or in the operational mode. The stop member may be axially displaceable with respect to the housing.

For switching the device into the reset mode, the stop member may be axially displaced with respect to the drive member such that the drive member and the stop member are brought out of mechanical cooperation, thereby permitting rotational movement of the drive member in the first rotational direction with respect to the housing and with respect to the stop member in the reset mode.

According to an embodiment, the assembly comprises a reset member. The reset member may be adapted and arranged to be moved, in particular axially moved, with respect to the housing between an operating position and a reset position. When the reset member is in the operating position, the drive member may, preferably permanently, mechanically cooperate with the stop member and the rotation member. When the reset member is in the operating position, the assembly is in the operational mode. When the reset member is in the reset position, the drive member may be prevented from mechanical cooperation with the stop member and/or the rotation member. Accordingly, when the reset member is in the reset position, the assembly is in the reset mode. When the reset member is in the reset position, the drive member may be rotatable in the first rotational direction with respect to the housing. Accordingly, the piston rod may be axially displaceable in the proximal direction with respect to the housing when the assembly is in the reset mode.

According to an embodiment, the stop member and the reset member are configured to mechanically cooperate, in particular to engage, with one another such that the stop member follows movement of the reset member towards the reset position. When the stop member follows movement of the reset member towards the reset position, the stop member may be brought out of mechanical cooperation with the drive member.

According to an embodiment, the assembly comprises a resilient reset member. In the operational mode, the resilient reset member may be configured to be biased thereby tending to move the reset member from the operating position into the reset position. For switching the assembly from the operational mode into the reset mode, the resilient reset member may be permitted to relax, thereby moving the reset member from the operating position into the reset position.

Accordingly, when the assembly is switched from the operational mode into the reset mode, the reset member may be automatically moved into the reset position by means of the resilient reset member.

According to an embodiment, the assembly may comprise a resilient operating member. The resilient operating member may be adapted and arranged to exert a force onto one, two or all of the drive member, the stop member and the rotation member. Said force may keep the drive member in, preferably permanent, mechanical cooperation with the stop member and the rotation member in the operational mode.

According to an embodiment, the resilient reset member is a reset spring member. The biasing member may be a biasing spring member. The resilient operating member may be an operating spring member. The spring strength of the reset spring member is preferably greater than the spring strength of the operating spring member. The spring strength of the operating spring member is preferably greater than the spring strength of the biasing spring member.

The force exerted by the reset spring member may overcome the force exerted by the operating spring member when the device is switched into the reset mode. Accordingly, disengaging the stop member and the drive member, when switching the assembly into the reset mode, may be facilitated.

According to an embodiment, the spring strength of the biasing spring member is great enough to achieve a relative movement between the rotation member and the drive member to bring said members out of mechanical cooperation.

Due to the biasing spring member, which is biased in the operational mode, the drive member and the rotation member may be automatically moved with respect to one another when the assembly is switched into the reset mode. The reset spring member and the biasing spring member, in combination, may facilitate provision of an assembly, which may be automatically switched into the reset mode.

According to an embodiment, in the reset mode, the stop member is secured to the housing by means of a, preferably releasable, connection preferably such that the stop member is prevented from axial movement in the proximal direction with respect to the reset member and/or with respect to the drive member.

Unintentional movement of the stop member which would bring the stop member and the drive member back into mechanical cooperation and, thus, for unintentionally switching the assembly from the reset mode back into the operational mode may be prevented in this way.

According to an embodiment, the assembly comprises a trigger member. The trigger member may be, preferably releasably, connectable to the housing. When the trigger member is connected to the housing, the trigger member may be arranged to prevent the resilient reset member from relaxing. Accordingly, when the trigger member is connected to the housing, the assembly is kept in the operational mode. When the trigger member is disconnected from the housing, the assembly may be switched from the operational mode into the reset mode.

Upon removing the trigger member, e.g. the cartridge and/or a cartridge holder of the device, the resilient reset member may be enabled to relax. The resilient reset member may drive movement of the reset member and, thus, of the stop member such that the stop member and the drive member are disengaged.

According to an embodiment, the housing comprises a guide track. The guide track may be adapted and arranged to mechanically cooperate with the trigger member to guide movement of the trigger member with respect to the housing when the trigger member is connected to or disconnected from the housing. The guide track may comprise a first section. The first section may run axially along a main longitudinal axis of the housing. The proximal end of the first section may define a proximal end position for the trigger member with respect to the housing. The guide track may comprise a second section. The second section may extend in an angular direction with respect to the main longitudinal axis of the housing. The first section may be connected to the second section. When movement of the trigger member is guided by the first section in the reset mode, e.g. when a replacement cartridge is introduced into the housing, mechanical cooperation between the stop member and trigger member may be prevented. When movement of the trigger member is guided by the second section in the reset mode, the trigger member and the stop member may be permitted to mechanically cooperate. The trigger member and the stop member may be adapted to mechanically cooperate to release the connection of the stop member to the housing for switching the assembly into the operational mode. In the operational mode, the stop member may be arranged to prevent rotation of the drive member in the first rotational direction, in particular for setting a dose. Thereby, the piston rod may be prevented from movement, in particular proximal movement, with respect to the housing during dose setting.

When the trigger member is guided by the second section, the trigger member may be rotatable with respect to the housing. When the trigger member is guided by the first section, rotation of the trigger member with respect to the housing may be prevented.

According to an embodiment, when the assembly is in the reset mode, energy is stored in the resilient operating member to drive movement of the stop member to switch the assembly into the operational mode.

In particular, when the reset member was moved back into the operating position in the reset mode, the resilient operating member may automatically bring the stop member and the drive member back into mechanical cooperation such that rotation of the drive member in the first rotational direction with respect to the stop member is prevented.

According to a preferred embodiment, an assembly for a drug delivery device is provided, comprising a housing having a distal end and a proximal end. The assembly comprises a rotation member adapted and arranged to be rotated in a first rotational direction and in a second rotational direction with respect to the housing in an operational mode of the assembly. The assembly comprises a drive member which is configured to mechanically cooperate with the rotation member such that the drive member follows rotation of the rotation member when the rotation member is rotated in the second rotational direction and such that the rotation member rotates with respect to the drive member when the rotation member is rotated in the first rotational direction. The assembly comprises a piston rod adapted and arranged to be driven in the distal direction with respect to the housing when the drive member is rotated in the second rotational direction. The assembly comprises at least one biasing member which is adapted and arranged to provide a force tending to bring the rotation member and the drive member out of mechanical cooperation in the operational mode. The assembly is switchable from the operational mode into a reset mode. For switching from the operational mode into the reset mode, the biasing member is configured to drive a relative axial movement between the drive member and the rotation member such that the rotation member and the drive member are brought out of mechanical cooperation.

The biasing member may be adapted and arranged to drive axial relative movement of the drive member with respect to the rotation member. Accordingly, the drive member and the rotation member are brought out of mechanical cooperation, in particular out of engagement. In the reset mode, the drive member may be rotatable in the first rotational direction. Accordingly, the piston rod may be rotatable and/or axially displaceable in the proximal direction with respect to the housing. In this way, provision of a resettable drug delivery device is facilitated.

Of course, features described above in connection with different aspects and embodiments may be combined with each other and with features described below.

Further features, advantages and refinements become apparent from the following description of the exemplary embodiments in connection with the accompanying figures.

BRIEF DESCRIPTION OF THE FIGURES

FIG. 3A shows a perspective side view of the drug delivery device of FIG. 2 in an operational mode after having dispensed a last dose, FIG. 3B shows a perspective sectional view of parts of the drug delivery device of FIG. 3A, FIG. 5A shows a perspective side view of the drug delivery device of FIG. 2 in a reset mode, FIG. 5B shows a perspective sectional view of parts of the drug delivery device of FIG. 5A, FIG. 6A shows a sectional side view of the drug delivery device of FIG. 5A, FIG. 6B shows a perspective sectional view of parts of the drug delivery device of FIG. 6A, FIG. 8A shows a sectional side view of the drug delivery device of FIG. 7A, FIG. 8B shows a perspective sectional view of parts of the drug delivery device of FIG. 8A.

DETAILED DESCRIPTION

Figure 1:
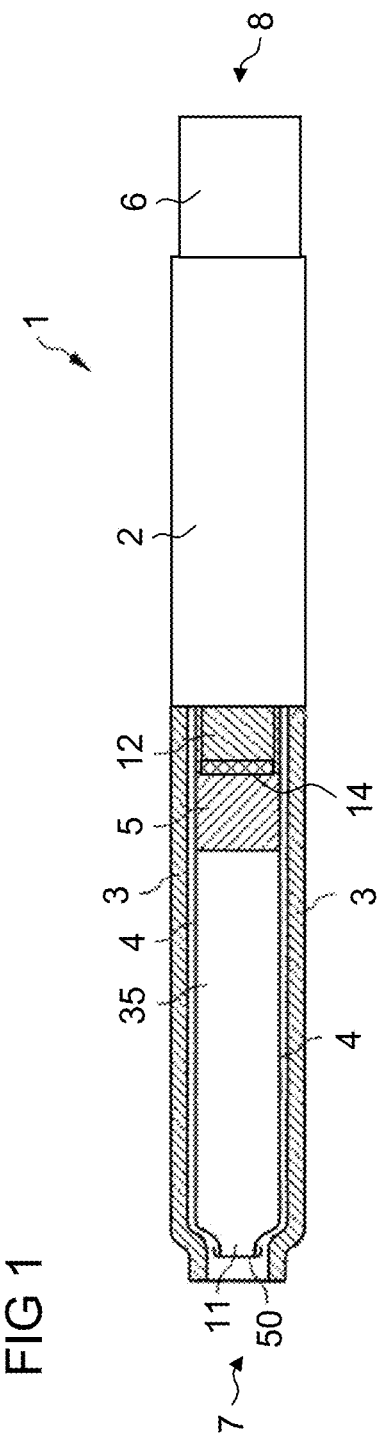
FIG. 1 schematically shows a perspective side view of an exemplary embodiment of a drug delivery device, FIG. 2 schematically shows a sectional side view of an exemplary embodiment of a drug delivery device.

Like elements, elements of the same kind and substantially equivalent or identically acting elements may be provided with the same reference numerals in the figures.

In FIG. 1 a drug delivery device 1 is shown. The drug delivery device 1 comprises a housing 2. The drug delivery device 1 and the housing 2 have a distal end 7 and a proximal end 8. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1.

The housing 2 may be designed to enable a safe and comfortable handling of the drug delivery device 1. The housing 2 may be configured to house, fix, protect or guide inner components of the drug delivery device 1, e.g. members of a drive mechanism which is explained later on in more detail. Preferably, the housing 2 limits or prevents the exposure of the inner components to contaminants such as liquid, dirt or dust. The housing 2 may be a unitary or a multipart component. The housing 2 may comprise a tubular shape, as shown in FIG. 1. Alternatively, the housing 2 may comprise a non-tubular shape.

The device 1 comprises a cartridge holder 3. The device 1 comprises a cartridge 4. The cartridge 4 is, preferably releasably, secured to the cartridge holder 3. The cartridge holder 3 stabilizes the cartridge 4 mechanically.

The cartridge holder 3 and the housing 2 may be, preferably releasably, secured to one another. For this purpose, a proximal end of the cartridge holder 3 may be secured to a distal end of the housing 2, e.g. by means of a bayonet fitting. A cartridge holder 3 which is releasably secured to the housing 2 may be detached from the housing 2, for example in order to allow for introducing a replacement cartridge into the device 1.

The cartridge 4 may hold a plurality of doses of a drug 35. The term "drug" as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

In a further embodiment the pharmaceutically active compound comprises at least one peptide for the treatment and/or prophylaxis of diabetes mellitus or complications associated with diabetes mellitus such as diabetic retinopathy.

In a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)$_5$des Pro36, Pro37, Pro38 [Asp28] Exendin-4 (1-39)-NH6,
des Pro36, Pro37, Pro38 [Asp28] Exendin-4(1-39)-(Lys)$_6$-NH2,
H-(Lys)6-des Pro36, Pro37, Pro38 [Asp28] Exendin-4(1-39)-(Lys)$_6$-NH2,
H-Asn-(Glu)5-des Pro36, Pro37, Pro38 [Asp28] Exendin-4 (1-39)-(Lys)$_6$-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2, H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)$_6$-NH2,
H-(Lys)6-des Pro36, Pro37, Pro38 [Trp(O2)25, Asp28] Exendin-4(1-39)-(Lys)$_6$-NH2,
H-Asn-(Glu)5-des Pro36, Pro37, Pro38 [Trp(O2)25, Asp28] Exendin-4(1-39)-(Lys)$_6$-NH2,
H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)$_6$-NH2,
H-(Lys)6-des Pro36, Pro37, Pro38 [Met(O)14, Asp28] Exendin-4(1-39)-(Lys)$_6$-NH2,
H-Asn-(Glu)$_5$ des Pro36, Pro37, Pro38 [Met(O)14, Asp28] Exendin-4(1-39)-(Lys)$_6$-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)$_6$-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)$_6$-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The drug delivery device 1 may comprise a needle assembly 10 (see FIG. 2), comprising a needle. The needle assembly 10 may be releasably attached to the cartridge holder 3. Alternatively, the drug delivery device 1 may be a needle-free device. The device 1 may comprise a cap 9 (see FIG. 2). The cap 9 may be adapted and arranged to cover the distal end of the device 1 including the cartridge holder 3 and, if applicable, the needle assembly 10 in a storage mode of the device 1.

The cartridge 4 comprises an outlet 11. The outlet 11 may be covered by a membrane 50. The membrane 50 may protect the drug 35 against external influences during storage of the cartridge 4. The cartridge 4 comprises a bung 5. The bung 5 is moveably retained in the cartridge 4. The bung 5 seals the cartridge 4 proximally. Movement of the bung 5 in the distal direction with respect to the cartridge 4 causes the drug 35 to be dispensed from the cartridge 4 through the outlet 11, provided that fluid communication was established between the interior and the exterior of the cartridge 4, e.g. when the membrane 50 is pierced by the needle.

The drug delivery device 1 may be an injection device. The drug delivery device 1 may be a pen-type device, in particular a pen-type injector. The device 1 may be a disposable or a re-usable device. The device 1 may be configured to dispense variable doses, in particular user-settable doses, of the drug 35. Alternatively, the device 1 may be configured to dispense fixed doses of the drug 35, in particular pre-set doses which may not be varied by the user. The drug delivery device 1 may be a manually, in particular a non-electrically, driven device.

The drug delivery device 1 comprises a piston rod 12. The piston rod 12 may be made of a flexible or a rigid material. The piston rod 12 may have a circular or a non-circular cross-section. The piston rod 12 may be a simple rod, a lead-screw, a rack, a pinion system or the like. The piston rod 12 may be of unitary or multipart construction.

The piston rod 12 operates through the housing 2 of the drug delivery device 1. The piston rod 12 is designed to transfer force to the bung 5, thereby driving the bung 5 in the distal direction with respect to the cartridge 4 and the housing 2. In this way, a dose of the drug 35 is dispensed from the cartridge 4 provided that the outlet 11 was opened, e.g. the membrane 50 was pierced by the needle as described above. The size of the dispensed dose is determined by the distance by which the bung 5 is displaced in the distal direction with respect to the housing 2.

A bearing member 14 is arranged between the bung 5 and the piston rod 12 to advance the bung 5. The bearing member 14 is displaceable together with the piston rod 12 with respect to the housing 2. The piston rod 12 is preferably rotatable with respect to the bearing member 14. In this way, the risk that the rotating piston rod 12 drills into the bung 5 and thereby damages the bung 5 is reduced. The bearing member 14 is axially locked to the piston rod 12. Accordingly, while the piston 12 rotates and is displaced with respect to the housing 2, the bearing member 14 is preferably only displaced, i.e. it does not rotate. Preferably, the bearing member 14 is snap-fitted to the piston rod 12.

The device 1 comprises a drive mechanism, which is explained later on in more detail. The drive mechanism is configured for transferring force, preferably user-exerted force, particularly preferably manually exerted force, to the bung 5 for displacing the bung 5 with respect to the cartridge 4 in the distal direction. A dose of the drug 35 may be dispensed from the cartridge 4 in this way.

Figure 2:
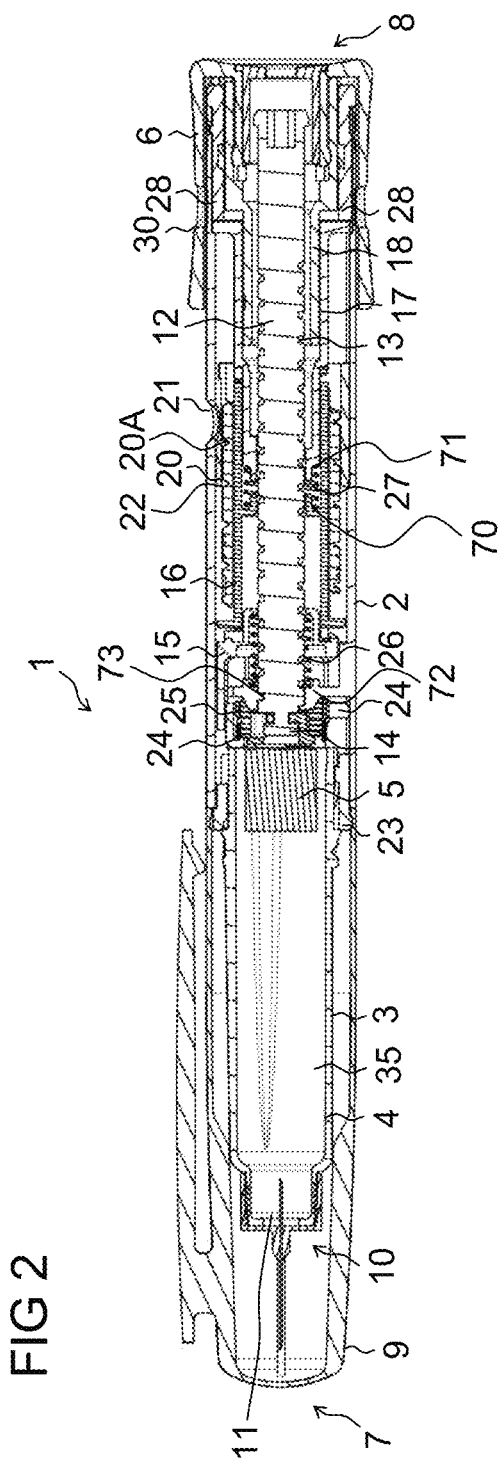
Figure 4A:
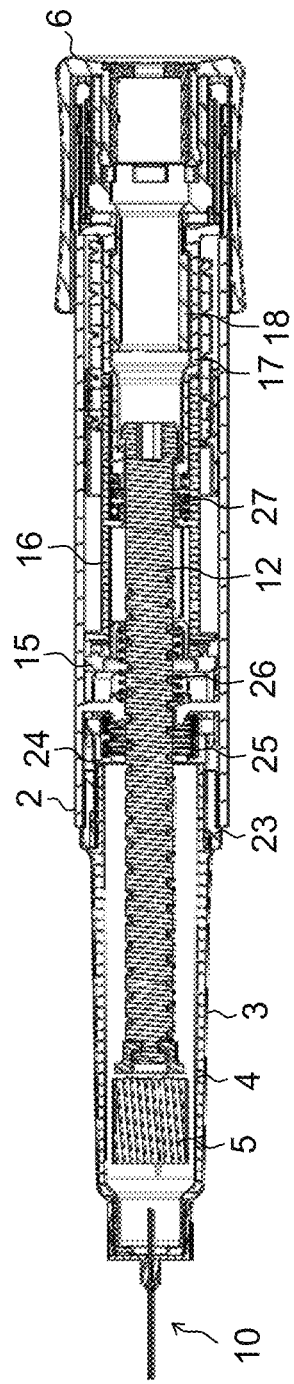
FIG. 4A shows a sectional side view of the drug delivery device of FIG. 3A.
Figure 4B:
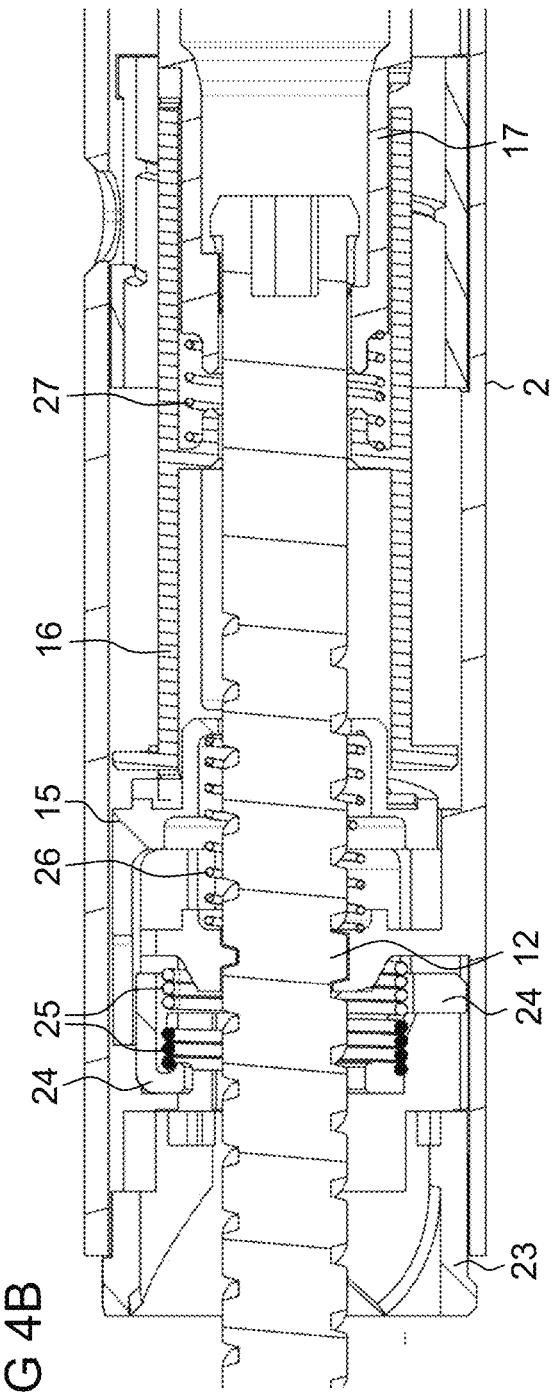
FIG. 4B shows a perspective sectional view of parts of the drug delivery device of FIG. 4A.
Figure 7A:
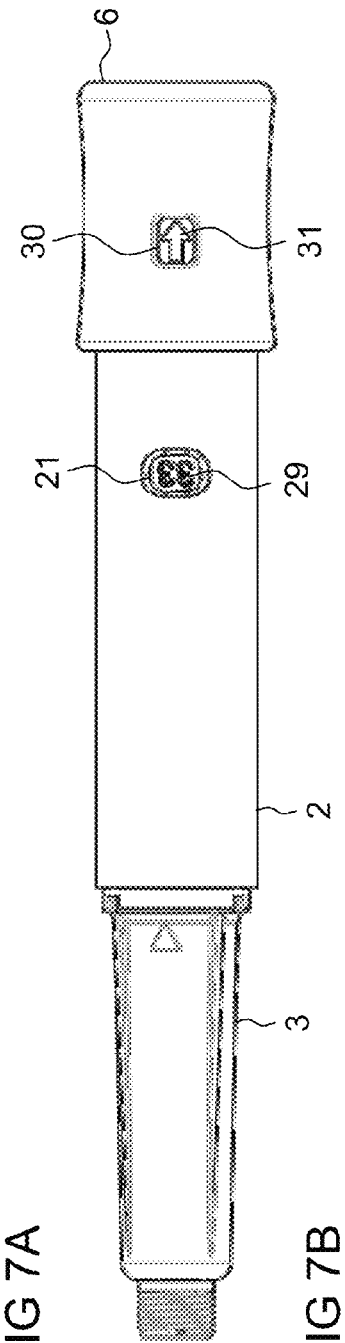
FIG. 7A shows a perspective side view of the drug delivery device of FIG. 2 in an operational mode before delivery of a first dose.
Figure 7B:
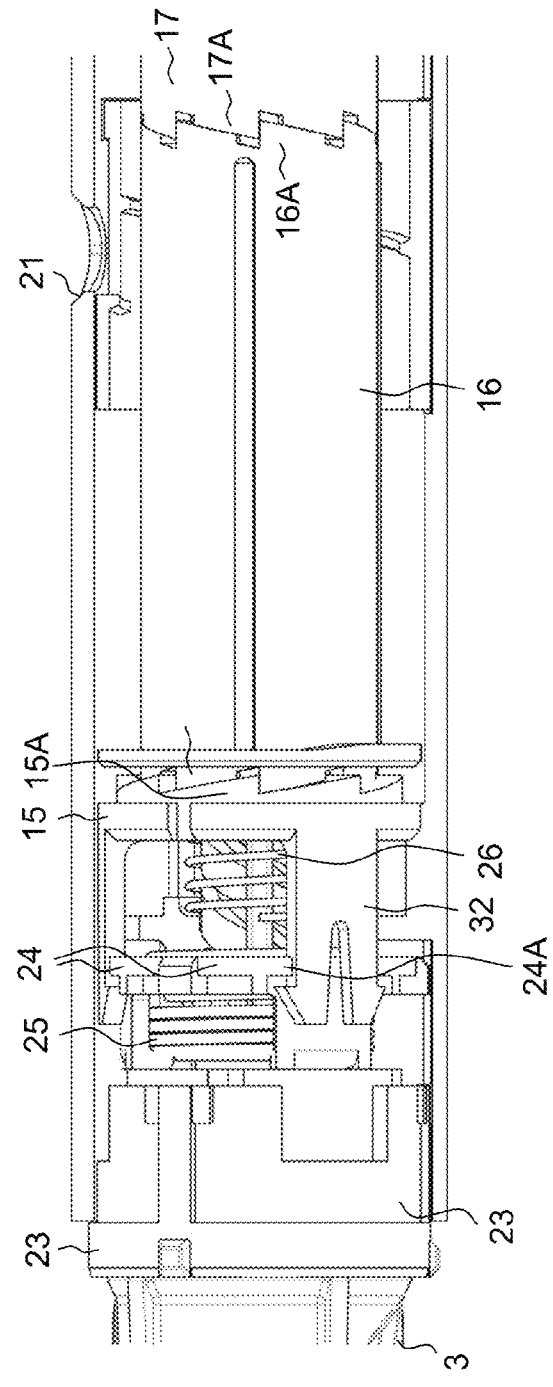
FIG. 7B shows a perspective sectional view of parts of the drug delivery device of FIG. 7A.

The drive mechanism comprises a dose member (see dose member 18 in FIG. 2). The dose member 18 may comprise or may be embodied as a sleeve. The dose member 18 is moveable with respect to the housing 2. The dose member 18 may be moveable in the proximal direction with respect to the housing 2 for setting a dose of the drug 35. The dose member 18 may be moveable in the distal direction with respect to the housing 2 for delivering the set dose. The distance by which the dose member 18 is displaced with respect to the housing 2 during setting of the dose may determine a size of the dose. The proximal end position and the distal end position of the dose member 18 may be determined by a respective stop element (see, for example proximal stop element 28 in FIG. 2) which may limit the proximal or distal travel of the dose member 18 with respect to the housing 2. The dose member 18 is prevented from being rotated with respect to the housing 2. In particular, the dose member 18 is prevented from rotation with respect to the housing 2 by mechanical cooperation of the dose member 18 and the housing 2. For example, the dose member 18 is splined to the housing 2.

The dose member 18 comprises a dose button 6. The dose button 6 is configured to be gripped by a user. The dose button 6 is arranged at the proximal end of the dose member 18. The dose button 6 is secured against movement with respect to the dose member 18. The dose button 6 may be connected to the dose member 18. Alternatively, the dose button 6 and the dose member 18 may be formed unitarily. The dose button 6 may comprise an aperture 30 (see FIG. 3A, for example) through which an action indication element 31 (see FIG. 3A) may be visible. Said indication element 31 may indicate a direction of movement of the dose member 18. Operation of the dose member 18 and of the drive mechanism in general is described in connection with FIG. 2.

FIG. 2 schematically shows a sectional side view of an exemplary embodiment of a drug delivery device.

The previously mentioned drive mechanism comprises a drive member 16. The drive member 16 is retained within the housing 3. The drive member 16 is configured to transfer force, preferably torque, to the piston rod 12. The transferred force causes the piston rod 12 to be displaced in the distal direction with respect to the housing 3 for dose delivery. The drive member 16 may be, at least in a limited fashion, rotatable with respect to the housing 2. The drive member may be, in a limited fashion, axially moveable with respect to the housing 3.

The drive member 16 is configured to engage the piston rod 12. Preferably, the drive member 16 is splined to the piston rod 12. Rotational movement of the drive member 16, for example rotational movement in a second rotational direction with respect to the housing 2, may be converted into movement of the piston rod 12 with respect to the housing 2. This is explained in more detail below.

The drive mechanism furthermore comprises a rotation member 17. In an operational mode of the device 1, e.g. in a dose setting and/or dose delivery mode of the device 1, the rotation member 17 is rotatable with respect to the housing 2 in a first rotational direction, in particular for setting of a dose, and in a second rotational direction, in particular for delivering the set dose. The second rotational direction is opposite to the first rotational direction. The first rotational direction may be counter-clockwise and the second rotational direction may be clockwise as seen from the proximal end of the device 1, for example.

The drive member 16, the rotation member 17 and/or the piston rod 12 are preferably configured to be rotatable about a common rotation axis. The rotation axis may extend through drive member 16, rotation member 17 and/or piston rod 12. The rotation axis may be the main longitudinal axis of the piston rod 12. The rotation axis may run between the proximal end and the distal end of the housing 2.

The rotation member 17 protrudes at least partly into the drive member 16. In the operational mode of the device 1, the rotation member 17 is coupled to the drive member 16 by a uni-directional clutch mechanism, in particular a friction clutch mechanism. This clutch mechanism permits rotational movement of the rotation member 17 with respect to the drive member 16 when the rotation member 17 rotates in the first rotational direction with respect to the housing 2. The clutch mechanism prevents rotational movement of the rotation member 17 with respect to the drive member 16, when the rotation member 17 rotates in the second rotational direction with respect to the housing 2. The drive member 16 may thus follow rotational movement of the rotation member 17 in the second rotational direction with respect to the housing 2.

In the operational mode, the drive member 16 is in direct mechanical contact, preferably permanent direct mechanical contact, with the rotation member 17. In the operational mode, the drive member 16 is arranged to abut and/or engage the rotation member 17. The drive member 16 comprises a toothing comprising a plurality of teeth 16A (see, for example FIG. 3B). Teeth 16A may be provided at one end of the drive member 16, e.g. its proximal end. The rotation member 17 comprises a toothing comprising a plurality of teeth 17A (see FIG. 3B). Teeth 16A and 17A may face one another. Teeth 17A may be provided at one end of the rotation member 17 which end faces the drive member 16, e.g. at the distal end of the rotation member 17. The teeth 16A may be circumferentially disposed on that end of the drive member 16 which faces the rotation member 17. The teeth 17A may be circumferentially disposed on the rotation member 17 at that end which faces the drive member 16.

Teeth 16A and/or 17A may extend and preferably may be oriented along the rotation axis. Teeth 16A and 17A may be configured to mate with one another. In the operational mode, the rotation member 17 and the drive member 16 may engage each other by teeth 16A and 17A.

A respective tooth of teeth 16A and/or teeth 17A may be ramp-shaped, in particular along the azimuthal (angular) direction as seen from the rotation axis. The ramp of the respective tooth is limited (in the angular direction) by a steep end face of that tooth, i.e. a face of the tooth that runs parallel to the rotation axis or includes a smaller angle with the rotation axis when projected on this axis than the ramp when projected on this axis. The steep end face is followed by the ramp of the next tooth.

When the steep end faces of two teeth 16A, 17A abut and the rotation member 17 is rotated further on in the second rotational direction, the steep sides stay in abutment and drive member 16 follows the rotation of rotation member 17. When the rotation member 17 rotates in the first rotational direction, the ramp of the teeth 16A, 17A—which ramps, in particular, run obliquely with respect to the rotation axis—slide along each other and, in consequence, the rotation member 17 may rotate with respect to the drive member 16.

The drive mechanism furthermore comprises a stop member 15. The drive member 16 may be arranged between the stop member 15 and the rotation member 17. In the operational mode of the device 1, the stop member 15 is configured for preventing rotational movement of the drive member 16 in the first rotational direction with respect to the housing 2 during setting of a dose, i.e. when the rotation member 17 rotates in the first rotational direction. Thus, the rotation member 17 may rotate in the first rotational direction with respect to the housing 2, whereas the drive member 16 and the stop member 15 are prevented from rotating.

In the operational mode, the drive member 16 is in direct mechanical contact, preferably permanent direct mechanical contact, with the stop member 15. In the operational mode, the stop member 15 is coupled to the drive member 16 by another uni-directional clutch mechanism, in particular a friction clutch mechanism. This clutch mechanism prevents rotational movement of the drive member 16 with respect to the stop member 15 when the rotation member 17 rotates in the first rotational direction with respect to the housing 2 in the operational mode. The clutch mechanism permits rotational movement of the drive member 16 with respect to the stop member 15, when the rotation member 17 rotates in the second rotational direction with respect to the housing 2 in the operational mode.

Thus, the rotation member 17 may rotate with respect to the drive member 16 and the stop member 15 in the first rotational direction during setting of the dose, with rotation of the drive member 16 being prevented by its interaction with the stop member 15. The rotation member 17 and the drive member 16 may rotate with respect to the stop member 15 in the second rotational direction during delivery of the dose.

The stop member 15 may be arranged to abut and/or engage the drive member 17 during setting of the dose and, preferably, during delivery of the dose, i.e. in the operational mode. The stop member 15 comprises a toothing having a plurality of teeth 15A (see FIG. 3B). Teeth 15A may be provided at one end of the stop member 15 which faces the drive member 16, e.g. its proximal end. The teeth 15A may be ramp-shaped with a steep side and a less steep ramp. The teeth 15A may be circumferentially disposed on the stop member 15. The teeth 15A may extend and preferably may be oriented along the rotation axis. The drive member 16 comprises a toothing having a plurality of teeth 16B (see FIG. 3B). Teeth 16B may be provided at one end of the drive member 16 which faces the stop member 15, e.g. the distal end of the drive member 16. The teeth 16B may extend and preferably may be oriented along the rotation axis. Teeth 16B and 15A are oppositely disposed. Teeth 16B may be configured in accordance with teeth 17A of the rotation member 17. Teeth 16A may be configured in accordance with teeth 15A of the stop member 15. Teeth 16B and 15A may face one another. Teeth 16B and 15A may mate with one another. Teeth 16B and 15A, in particular the steep sides of the teeth are configured to abut for preventing rotation of the drive member 16 with respect to the housing 2 and, in particular, with respect to the stop member 15 in the first rotational direction in the operational mode.

The stop member 15 is, preferably permanently, secured against rotational movement with respect to the housing 2. Axial displacement of the stop member 15 with respect to the housing 2 may be allowed in a limited fashion. Preferably, the stop member 15 is splined to the housing 2. Slight axial movement of the stop member 15 may compensate for play between components of the drive mechanism in the operational mode which is explained below in more detail. Furthermore, axial movement of the stop member 15 may enable switching the device 1 from the operational mode into a reset mode of the device, e.g. a mode in which the device 1 is reset, in particular in which the piston rod 12 is moved proximally towards a proximal starting position, which is explained later on in more detail.

From the group comprising drive member 16, stop member 15 and rotation member 17 one or more members, preferably two members or three members, may be in a limited fashion axially displaceable with respect to the housing 2 and, preferably, with respect to the piston rod 12 in the operational mode of the device 1. Therein, the drive member 16 and another one of the recited members may be axially displaceable with respect to the housing 2. The remaining member may be secured against axial displacement or may also be axially displaceable during operation of the device 1. Accordingly, if the drive member 16 and the stop member 15 are axially displaceable in the operational mode, the rotation member 17 may be axially secured or axially displaceable and so on. Play between the components caused by relative (axial) movement of components of the clutch mechanism with respect to the housing 2 can be compensated for in this way. The distance by which the respective components may be axially displaced with respect to the housing 2 may correspond to the maximum depth of a tooth of the respective toothing 16A or 16B of the drive member 16. Alternatively, the distance may be greater than the maximum depth of a respective tooth 16A, 16B.

The drive mechanism comprises a biasing member 27. Biasing member 27 may comprise helical spring member. Biasing member 27 may comprise a compression spring. The biasing member 27 may be biased in the operational mode of the device 1. The biasing member 27 is configured to provide a force tending to bring the drive member 16 and the rotation member 17 out of mechanical cooperation in the operational mode. The force may be exerted along the rotation axis. The force may be exerted in the distal and/or proximal direction. In particular, in the operational mode, the biasing member 27 may tend to force the rotation member 17 and the drive member 16 away from each other in opposite axial directions. In particular, the biasing member 27 may tend to force the drive member 16 in the distal direction with respect to the rotation member 17. The biasing member 27 may tend to force the rotation member 17 in the proximal direction with respect to the drive member 16.

The biasing member 27 may be arranged within the drive member 16. The biasing member 27 is located between a collar 70 and a collar 71 of the device 1 as shown in FIG. 2. The biasing member 27, in particular the two ends of the biasing member 27, may be arranged in a respective groove (not explicitly shown) arranged within the respective collar 70, 71. Collar 70 may be part of the drive member 16. Preferably, collar 70 is formed unitarily with the drive member 16. Collar 71 may be part of the rotation member 17. Preferably, collar 71 is formed unitarily with the rotation member 17. Collar 71 may be arranged in the distal end section of the rotation member 17. The biasing member 27 abuts a proximal end face of the collar 70 and the distal end face of collar 71. The biasing member 27 thus provides a separating force on the drive member 16 and the rotation member 17.

Furthermore, the drive mechanism comprises a resilient operating member 26. The resilient operating member 26 may be a spring member. The resilient operating member 26 may be a helical spring, preferably helical coil spring. The resilient operating member 26 may be a compression spring. The resilient operating member 26 may be integrated within stop member 15 or may be a separate component. The resilient operating member 26 may be arranged on the distal side of the stop member 15.

The resilient operating member 26 may be biased in the operational mode of the device 1. The resilient operating member 26 may be biased in the reset mode of the device 1. The resilient operating member 26 may provide a force that tends to keep the drive member 16, the rotation member 17 and the stop member 15 in, preferably permanent, mechanical contact, e.g. in abutment, with each other in the operational mode of the device 1. The force may be exerted along the rotation axis. The force may be exerted in the proximal direction.

The spring strength of the resilient operating member 26 may be greater than the spring strength of the biasing spring member 27 such that the force which tends to separate the drive member 16 and the rotation member 17 is overcome in the operational mode. In particular, the spring strength of the resilient operating member 26 may be great enough such that permanent mechanical cooperation of the drive member 16, the stop member 15 and the rotation member 17 may be enabled in the operational mode.

The drive mechanism furthermore comprises a support member (not explicitly shown). Support member is expediently fixed against axial and rotational movement with respect to the housing 2. Support member is arranged on that side of the drive member 16 which is remote from the stop member 15. Support member may be a protrusion, for example a ring-like protrusion. Rotation member 17 may extend through an opening in support member. The support member may provide for a counter force to the force which is exerted by the resilient operating member 26. Permanent abutment of the rotation member 27 with the drive member 16 and of the drive member 16 with the stop member 15 in the operational mode, e.g. during setting and delivering of a dose of the drug 35, may be facilitated in this way.

The rotation member 17 may comprise a, preferably radially, outwardly protruding member (not explicitly shown), for example a flange portion. The protruding member is expediently provided for abutting support member, in particular the distal side of support member.

A support 72 may be provided for providing a counterforce to the force exerted by the resilient operating member 26. In particular, support 72 prevents relaxation of the resilient operating member 26 in the reset mode of the device 1, which is explained later on in more detail. Support 72 may be arranged on that side of the drive member 16 which is remote from the rotation member 17. Support 72 may be arranged on that side of the stop member 15 which is remote from the support member. The support 72 may be arranged to abut the resilient operating member 26. The support 72 may be secured against axial and rotational movement with respect to the housing 2. Preferably, support 72 is formed unitarily with the housing 2.

The drive mechanism furthermore comprises the previously described dose member 18. In the operational mode of the device 1, the dose member 18 is moveable with respect to the housing 2 in the proximal direction for setting a dose of the drug 35. In the operational mode of the device 1, the dose member 18 is moveable with respect to the housing 2 in the distal direction for delivering the set dose of the drug 35. The dose member 18 may engage the housing 2. The dose member 18 is preferably secured against rotational movement with respect to the housing 2. The dose member 18 may comprise a guide feature, for example a guide lug or a guide slot (not explicitly shown). The guide feature may be configured to engage a further guide feature, for example a guide slot or a guide lug, which is provided on an inner surface of the housing 2. In this way, rotational movement of the dose member 18 with respect to the housing 2 may be prevented.

The dose member 18 may be moveable in the proximal direction and in the distal direction with respect to rotation member 17. The dose member 18 is, preferably permanently, coupled to rotation member 17 such that movement of the dose member 18 in the proximal direction with respect to the housing 3, e.g. for setting a dose of the drug 35, is converted into rotational movement of the rotation member 17 in the first rotational direction. Movement of the dose member 18 in the distal direction with respect to the housing 2, e.g. for delivering the set dose, is converted into rotational movement of the rotation member 17 in the second rotational direction.

The rotation member 17 is arranged inside the dose member 18. The rotation member 17 may be provided with an outer thread (not explicitly shown). The outer thread may be engaged with one of or a plurality of engagement members of the dose member 18. The respective engagement member is arranged on the inside of the dose member 18. The respective engagement member may be a thread or a part of a thread, for example. Thus, dose member 18 and rotation member 17 are threadedly coupled, in particularly threadedly engaged.

The rotation member 17, the drive member 16, the stop member 15 and the dose member 18 may comprise or may be embodied as a respective sleeve. The piston rod 12 may be arranged to be driven and, in particular, may be driven through one of, more of or all of those sleeves. The piston rod 12 may run through one of, more of or all of those sleeves.

The drive member 16 and the piston rod 12 are configured for rotational movement of the drive member 16 with respect to the housing 2 being converted into rotational movement of the piston rod 12 with respect to the housing 2. The drive member 16 may engage the piston rod 12. The piston rod 12 is displaceable with respect to the drive member 16 along a displacement axis, preferably the rotation axis. The drive member 16 may be splined to the piston rod 12, for example.

The piston rod 12 comprises an outer thread 13. The piston rod 12 is threadedly coupled to the housing 2. The piston rod 12 may extend through and may be engaged with a (part) thread 73 in an opening which is provided in the housing 2, for example in support 72.

The piston rod 12 comprises an engagement track 55 (see FIG. 11), preferably two oppositely disposed engagement tracks 55. Engagement track 55 is arranged on an outer surface of the piston rod 12. The respective engagement track 55 may interrupt thread 13. The respective engagement track 55 preferably extends along the axis along which the piston rod 12 is displaceable with respect to the housing 2 and, in particular, with respect to the drive member 16. Via engagement track 55, the piston rod 12 mechanically cooperates with, in particular is splined to, the drive member 16. For this purpose, a lug provided inside of the drive member 16 may engage the engagement track 55 (not explicitly shown).

Rotational movement of the drive member 16 with respect to the housing 2 may thus be converted into rotational movement of the piston rod 12 with respect to the housing 2. Rotational movement of the piston rod 12 is, on account of the threaded engagement of the piston rod 12 and the housing 2, may be converted into movement of the piston rod 12 with respect to the housing 2 in the distal direction for dispensing the set dose in the operational mode of the device 1.

The device 1 comprises a number sleeve 20 (see FIGS. 2 and 6B). Preferably, the number sleeve 20 is splined to the drive member 16. The number sleeve 20 may comprise a thread 20A arranged on an outer surface of the number sleeve 20. Thread 20A may be configured to mechanically cooperate with a thread 22 provided on an inner surface of housing 2. The number sleeve 20 may be adapted to register the axial position of the piston rod 12 with respect to the housing 2 for indicating the number of doses of the drug 35 remaining in the cartridge 4. The number of remaining doses may, for example, be indicated by displaying a dose indicator element 29 (see FIGS. 3A and 10, for example), which may be located on an outer surface of the drive member 16, through an aperture 21 (see FIG. 3A) in the housing 2, for example.

In the following, operation of the drive mechanism for delivering a dose of the drug 35 from the cartridge 4 is described.

To set a dose, a user may manually move dose member 18 in the proximal direction with respect to the housing 2. To do so, the user may grip dose button 6 and pull it in the proximal direction. Dose member 18 moves proximally also with respect to the rotation member 17. Proximal movement of the rotation member 17 is prevented by the previously described support member which abuts the protruding member of rotation member 17. Consequently, the proximal movement of dose member 18 with respect to the housing 2 is converted into rotational movement of the rotation member 17 in the first rotational direction with respect to the housing 2, in particular on account of the threaded engagement of dose member 18 and rotation member 17. Thus, the rotation member 17 rotates in the first rotational direction—counter-clockwise as seen from the proximal end of the rotation member 17—with respect to the housing 2. Rotation member 17 also rotates with respect to the drive member 16 and to the stop member 15. The drive member 16 is prevented from rotating in the first rotational due to mechanical cooperation with the stop member 15, e.g. by interlocking of teeth 16B and 15A. As the piston rod 12 is coupled to the drive member 16 and rotation in the first rotational direction of the drive member 16 would cause the piston rod 12 to travel in the proximal direction, the piston rod 12 is prevented from being driven in the proximal direction by mechanical cooperation of stop member 15 and drive member 16 in the operational mode. By preventing the piston rod 12 from moving during dose setting dose accuracy can be increased.

When the rotation member 17 rotates in the first rotational direction, the ramps of the teeth 17A of rotation member 17 slide along the ramps of the teeth 16A of the drive member 16. Thus, a tooth 17A of the rotation member 17 may index around the rotation axis until the tooth 17A engages one of the next teeth 16A of drive member 16. The teeth 17A of rotation member 17 slide along the ramps of the teeth 16A of drive member 16. During this movement, drive member 16 and, in particular, stop member 15 are displaced along the rotation axis with respect to piston rod 12 and the housing 2 by a distance determined by, preferably equal to, the depth of a tooth 16A, before a tooth 17A (totally) disengages that tooth 16A. Afterwards, the tooth 17A of the rotation member 17 engages the next tooth 16A and the force provided by resilient operating member 26 moves drive member 16 and, in particular, stop member 15 back along the rotation axis into the axial start position. A tooth 17A of the rotation member 17 which engages the next tooth 16A of the drive member 16 may cause an audible and/or tactile feedback to the user.

The drive mechanism may be suitable for a fixed dose device or a user settable dose device. The size of the fixed dose of the drug 35 which is to be delivered or the increments in which a user-settable dose may be varied by a user are preferably determined by the distribution of the teeth of the drive member 16, the rotation member 17 and the stop member 15. The rotation member 17 may be rotated over more than one tooth 16A (dose increment) of the drive member 16 for a user-settable dose device and over one tooth 16A (only) for a fixed dose device. The number of teeth 16A in the drive member 16 over which the rotation member 17 rotates during dose setting determines the size of the dose which is actually delivered. The dose member 18 and the rotation member 17 may be adapted to mechanically cooperate with one another such that the rotation member 17 may rotate only by one tooth 17A for a fixed dose device and by more than one tooth 17A for a variable dose device.

After the dose has been set, the dose member 18 is moved by the user in the distal direction with respect to housing 2. The rotation member 17 accordingly rotates in the second rotational direction, which is opposite to the first rotational direction, with respect to the housing 2. Drive member 16 follows rotational movement of the rotation member in the second rotational direction. Rotational movement of the drive member 16 in the second rotational direction is converted into rotational movement of the piston rod 12 in the second rotational direction, which movement, in turn, is converted into movement of the piston rod 12 in the distal direction. Accordingly, the bung 5 may be displaced in the distal direction with respect to the cartridge 4 and a dose of the drug 35 is dispensed from the cartridge 4 the amount of which corresponds to the previously set dose.

During dose delivery, teeth 16A and 17A interlock and ramps of the teeth 16B of the drive member 16 slide along ramps of the teeth 15A of the stop member 15. This movement is similarly as described above for the relative rotational movement of rotation member 17 and drive member 16 with opposite rotation direction. The stop member 15 is thereby displaced in the distal direction with respect to the drive member 16 by a distance corresponding to the depth of a tooth 15A in stop member 15. Resilient operating member 26 forces the stop member 15 back into the axial starting position, when the next tooth 15A is engaged by the respective tooth 16B. A tooth 16B of the drive member 16 which engages the next tooth 15A of the stop member 15 may cause an audible and/or tactile feedback to the user.

The operation for setting and delivering of a dose may be repeated until a last dose of the drug 35 held in the cartridge 4 was dispensed, which is indicated in FIG. 3A, for example. When the last dose has been dispensed, the device 1 may be switched from the operational mode into the reset mode for resetting the device 1 for enabling delivery of a plurality of doses of a drug held in a replacement cartridge.

For resetting the device 1, the piston rod 12 has to be displaced in the proximal direction with respect to the housing 2 towards a proximal starting position. Accordingly, the drive member 16, which is preferably permanently splined to the piston rod 12, would have to be rotatable in the first rotational direction. However, the piston rod 12 is prevented from proximal movement due to mechanical interaction of the drive member 16 and the stop member 15 in the operational mode of the device 1. Accordingly, for resetting the device 1, the drive member 16 and the stop member 15 have to be brought out of mechanical cooperation. Furthermore, for resetting the device 1, the drive member 16 and the rotation member 17 have to be prevented from mechanical cooperation to enable rotational movement of the drive member 16 in the first rotational direction with respect to the rotation member 17.

In the reset mode of the device 1, the drive member 16 and the stop member 15 as well as the drive member 16 and the rotation member 17 are brought out of mechanical cooperation to enable rotational movement of the drive member 16 in the first rotational direction and, thus, movement of the piston rod 12 in the proximal direction towards the proximal starting position of the piston rod 12. In the reset mode, direct mechanical contact of the drive member 16 with the rotation member 17 is prevented. In the reset mode, direct mechanical contact of the drive member 16 with the stop member 15 is prevented, as well. Operation of resetting the device 1 is described later on in more detail.

The device 1 comprises a reset member 24. The reset member 24 is axially moveable with respect to the housing 2. The reset member 24 is, at least in a limited fashion, axially moveable with respect to the stop member 15. Axial movement of the reset member 24 in the distal direction may be at least partially transferred into axial movement of the stop member 15 for bringing the stop member 15 and the drive member 16 out of mechanical cooperation, thus switching the device 1 into the reset mode. The reset member 24 is, preferably permanently, secured against rotation with respect to the housing 2 and with respect to the stop member 15. Preferably, the reset member 24 is splined to the housing 2. The stop member 15 may be splined to the housing 2. Alternatively, one of the reset member 24 and the stop member 15 may be splined to the housing 2. The other one of the reset member 24 and the stop member 15 may be splined to the member which is splined to the housing 2 in order to secure the stop member 15 and the reset member 24 against rotation with respect to the housing 2.

The reset member 24 may be arranged in the distal end section of the housing 2. The reset member 24 may comprise a ring-like structure. The reset member 24 may comprise or may be embodied as a sleeve through which the piston rod 12 travels. The reset member 24 comprises one, preferably two or more, guide members 24C (see, for example, FIG. 3B). The respective guide member 24C protrudes distally from the reset member 24. The guide members 24C are preferably circumferentially disposed around the reset member 24.

For switching the device 1 from the operational mode into the reset mode, the reset member 24 is axially moved with respect to the housing 2 and with respect to the drive member 16 from an operating position towards a reset position.

When the reset member 24 is in the operating position, the drive member 16 mechanically cooperates with the stop member 15 and the rotation member 17. Accordingly, when the reset member 24 is in the operating position, the device 1 is in the operational mode. When the reset member 24 is in the reset position, the drive member 16 may be prevented from mechanical cooperation with the stop member 15 and the rotation member 17. Accordingly, when the reset member 24 is in the reset position, the device 1 is in the reset mode.

The operating position may be more proximal with respect to the housing 2 than the reset position. In the operational mode, the reset member 24, in particular a distal face of the reset member 24, is configured to mechanically cooperate with, in particular to abut with, the cartridge 4 and/or the cartridge holder 3. In particular, when the reset member 24 is in the operating position, the respective guide member 24C abuts a proximal face of the cartridge 4 or the cartridge holder 3 for preventing movement of the reset member 24 with respect to the housing 2 in the distal direction the operational mode.

The device 1 comprises a securing member 23. The securing member 23 is adapted and arranged for securing the cartridge 4 and/or the cartridge holder 3 to the housing 2 of the device 1 which is described later on in more detail. The securing member 23 may be adapted and arranged to receive at least partly the reset member 24 in the reset mode of the device 1. The securing member 23 may be configured to provide a distal end stop for the reset member 24 when the reset member 24 is moved into the reset position.

When the reset member 24 is in the reset position, the securing member 23, in particular a proximal face of the securing member 23, may abut the reset member 24. The reset member 24 may comprise a flange 24A (see FIG. 3B, for example). Flange 24A may protrude radially outwardly from the reset member 24. Due to mechanical cooperation of the securing member 23 and said flange 24A further movement of the reset member 24 in the distal direction may be prevented when the reset member 24 is in the reset position. Accordingly, the securing member 23 is adapted and arranged to limit the distal movement of the reset member 24 and, hence, of the stop member 15 when the device 1 is switched into the reset mode.

The securing member 23 comprises one, preferably two or more, receiving elements 23A (see, for example, FIGS. 3B and 5B). The respective receiving element 23A is adapted and arranged to receive a distal portion of the stop member 15 in the reset mode of the device 1, which is explained later on in more detail. The respective receiving element 23A is adapted and arranged to receive the respective guide member 24C of the reset member 24 in the reset mode of the device 1.

The securing member 23 may comprise or may be embodied as a sleeve. The securing member 23 is secured against axial and rotational movement with respect to the housing 2. Alternatively, the securing member 23 is formed unitarily with the housing 2.

In the operational mode, the reset member 24 is prevented from mechanical cooperation, in particular engagement, with the stop member 15. The reset member 24 is adapted and arranged to mechanically cooperate with the stop member 15 when the device 1 is switched into the reset mode. The reset member 24 may be configured to engage with the stop member 15 when the device 1 is switched from the operational mode into the reset mode, such that axial, in particular distal, movement of the reset member 24 is transferred into distal movement of the stop member 15 with respect to the housing 2 for bringing the stop member 15 and the drive member 16 out of mechanical cooperation.

The reset member 24 may comprise at least one, preferably two, recesses 24B (see FIG. 3B). The two recesses 24B may be arranged oppositely with respect to one another. The stop member 15 comprises at least one, preferably two or more, such as three, interaction features 32 (see FIG. 3B). The respective interaction feature 32 may protrude from the stop member 15, in particular from a main body of the stop member 15, in the distal direction. The respective interaction feature 32 extends parallel with respect to the rotation axis. The respective interaction feature 32 may be adapted and arranged to be received at least partially by the securing member 23, in particular by the receiving member 23A, in the reset mode of the device 1.

The respective interaction feature 32 may be an assembling feature. The respective interaction feature 32 comprises two legs 32A, 32B. Legs 32A, 32B extend parallel with respect to each other and with respect to the rotation axis. The respective interaction feature 32 is guided through the respective recess 24B of the reset member 24. By means of legs 32A, 32B, the stop member 15 may be operatively connected, e.g. snap-fitted, to the reset member 24 when the device 1 is assembled.

The respective interaction feature 32 is configured to provide retaining faces 80A, 80B. The retaining faces 80A, 80B are configured to mechanically cooperate with the reset member 24 when the device 1 is switched into the reset mode. The retaining faces 80A, 80B are arranged in the distal end section of the interaction feature 32, in particular of legs 32A, 32B. In particular, the retaining faces 80A, 80B are arranged distally offset from the, preferably ring-like, main body of the stop member 15A. The retaining faces 80A, 80B extend transversally with respect to the rotation axis.

As described above, the stop member 15, in particular the retaining faces 80A, 80B, may be adapted to mechanically cooperate with the reset member 24 when the reset member 24 is moved distally for switching the device 1 from the operational mode into the reset mode. Upon mechanical cooperation of the stop member 15 and the reset member 24, axial movement of the reset member 24 is transferred into movement of the stop member 15 for disengaging the stop member 15 and the drive member 16.

Furthermore, the device 1 comprises a resilient reset member 25. Resilient reset member 25 may comprise a spring member, like a coil spring and/or a compression spring, for example. Resilient reset member 25 may comprise a compression spring. The resilient reset member 25 may be biased in the operational mode of the device 1. In particular, the resilient reset member 25 may be biased when the reset member 24 is in the operating position. The resilient reset member 25 may be fully or at least partly relaxed when the reset member 24 is in the reset position, i.e. when the device 1 is in the reset mode. The resilient reset member 25 may be configured to provide a force tending to move the reset member 24 from the operating position into the reset position, i.e. for switching the device 1 into the reset mode, thereby bringing the drive member 16 and the stop member 15 out of mechanical cooperation. When the device 1 is in the operational mode, this force is counteracted by the proximal end of the cartridge 4 and/or the cartridge holder 3 which is secured to the housing 2.

The spring strength of the resilient reset member 25 is preferably greater than the spring strength of the previously described resilient operating member 26. Thus, when the device 1 is switched into the reset mode, the resilient reset member 25 may exert a force on the reset member 24 which overcomes the force exerted by the resilient operating member 26 which tends to keep the stop member 15, the rotation member 17 and the drive member 16 in abutment and/or engagement. In particular, the force provided by the resilient operating member 26 to hold the drive member 16, the stop member 15 and the rotation member 17 in abutment, may be at least decreased or fully removed in the reset mode due to disengagement of the stop member 15, the drive member 16 and/or the rotation member 17. The force of the resilient operating member 26 may be decreased such that the spring strength of the biasing member 27 is great enough to achieve a relative movement between the rotation member 17 and the drive member 16 to bring said members out of mechanical cooperation for switching the device 1 into the reset mode.

Switching the device 1 from the operational mode into the reset mode and resetting the device 1 is described in connection with FIGS. 3A through 8B.

FIGS. 3A, 3B, 4A and 4B show the device 1 in the operational mode after having dispensed the last dose. Accordingly, zero remaining doses are indicated by the dose indicator element 29. The piston rod 12 is arranged in a distal end position (see FIGS. 4A and 4B).

The stop member 15 and the drive member 16 are still in mechanical cooperation as shown in FIG. 3B. The same applies for the drive member 16 and the rotation member 17. The stop member 15 is prevented from mechanical cooperation with the reset member 24. In particular, the respective retaining face 80A, 80B of the interaction feature 32 of the stop member 15 is arranged at a distance from the reset member 24. The resilient reset member 25, the resilient operating member 26 and the biasing member 27 are in a biased condition, as can be seen from FIG. 4B.

The user may now manually remove the cartridge holder 3 holding the cartridge 4 (see FIGS. 5A, 5B, 6A and 6B). Alternatively, in case the cartridge 4 is secured directly to the housing 2, the user may remove the cartridge 4. This is described in more detail in the following.

Figure 10:
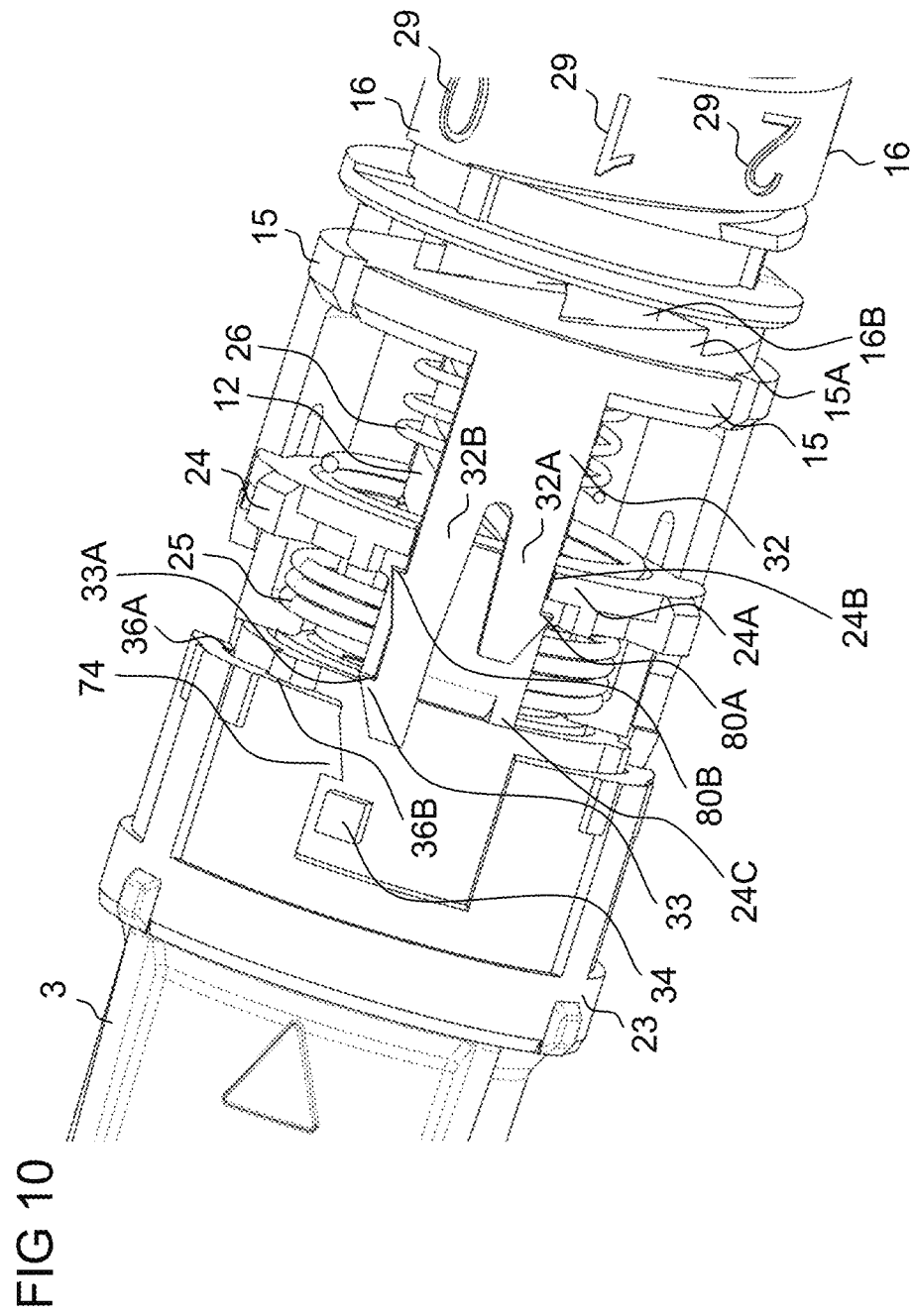
FIG. 10 shows a perspective side view of parts of a drug delivery device according to a further embodiment in the operational mode.

The housing 2, in particular the securing member 23, may comprise a guide track 36A, 36B (see FIG. 10). The guide track 36A, 36B may be arranged on an inner surface of the securing member 23. The guide track 36A, 36B may be adapted and arranged to mechanically cooperate with a corresponding guide feature (not explicitly shown) arranged at the outer side of the cartridge 4 and/or the cartridge holder 3 in order to guide the movement of the cartridge 4 or the cartridge holder 3 with respect to the housing 2 when connecting or disconnecting the cartridge and/or the cartridge holder 3 from the housing 2.

The guide track may comprise a first section 36A. The guide track may comprise a second section 36B. The first section 36A is connected to the second section 36B. The second section 36B extends in an angular direction. The first section 36A extends axially, e.g. parallel to the main longitudinal axis of the housing 2. The proximal end of the first section 36A is configured to define a proximal end position for the cartridge 4 and/or the cartridge holder 3 with respect to the housing 2, when the cartridge 4 or the cartridge holder 3 is attached to the housing 2 due to the guide feature abutting a proximal side-wall of the first section 36A.

For removing the cartridge 4 or the cartridge holder 3 movement of the cartridge 4 or the cartridge holder 3 is initially guided by the second section 36B. Accordingly, the cartridge 4 or the cartridge holder 3 is at first rotated with respect to the housing 2 without being moved axially. The cartridge 4 or the cartridge holder 3 is rotated until it reaches the first section 36A, in particular a transition region of the first section 36A and the second section 36B. The cartridge 4 or the cartridge holder 3 may now be axially, in particular distally, moveable with respect to the housing 2, the movement being guided by the first section 36A.

When the cartridge 4 or the cartridge holder 3 is moved distally, the resilient reset member 25 is permitted to relax (see FIG. 6B) as the cartridge 4 or the cartridge holder 3 no longer counteracts the force exerted by the resilient reset member 25 in the distal direction. The resilient reset member 25 acts on the reset member 24. Accordingly, the resilient reset member 25 automatically moves the reset member 24 in the distal direction from the operating position towards the reset position. Thereby, the reset member 24 is moved relative to the stop member 15. In particular, the reset member 24 is moved towards the respective retaining face 80A, 80B of interaction element 32. The reset member 24 is moved until it is in abutment with the respective retaining face 80A, 80B (FIG. 5B).

When the reset member 24 is moved further towards the reset position, distal movement of the reset member 24 is transferred into distal movement of the stop member 15 with respect to the drive member 16 due to mechanical cooperation of the respective retaining face 80A, 80B and the reset member 24. Accordingly, the stop member 15 and the drive member 16 are brought out of mechanical cooperation (FIG. 5B). The distance by which the stop member 15 is moved distally with respect to the drive member 16 has to be at least equal to, preferably greater than, the depth of a respective tooth 16B of the drive member 16 to bring the drive member 16 and the stop member 15 out of mechanical cooperation, in particular to disengage teeth 16B and 15A.

When the stop member 15 and the drive member 16 are moved out of mechanical cooperation, the force provided by the resilient operating member 26 which tends to keep the drive member 16 in cooperation with the stop member 15 and the rotation member 17 is decreased. Accordingly, the biasing member 27 is permitted to relax (see FIG. 6B) at least partially. The biasing member 27 acts on the drive member 16 and the rotation member 17, thus automatically gradually moving the drive member 16 and the rotation member 17 relatively to each other for bringing said members out of mechanical cooperation (FIG. 5B). In particular, the drive member 16 may be driven in the distal direction with respect to the rotation member 17. Distal movement of the drive member 16 may be limited by a respective distal stop feature (not explicitly shown). The rotation member 17 may be driven in the proximal direction with respect to the drive member 16. Proximal movement of the rotation member 17 may be limited by a respective proximal stop feature (not explicitly shown). The distance by which the drive member 16 and the rotation member 17 are driven relatively to each other is at least equal to, preferably greater than the depth of a respective tooth 16A of the drive member 16.

Figure 9:
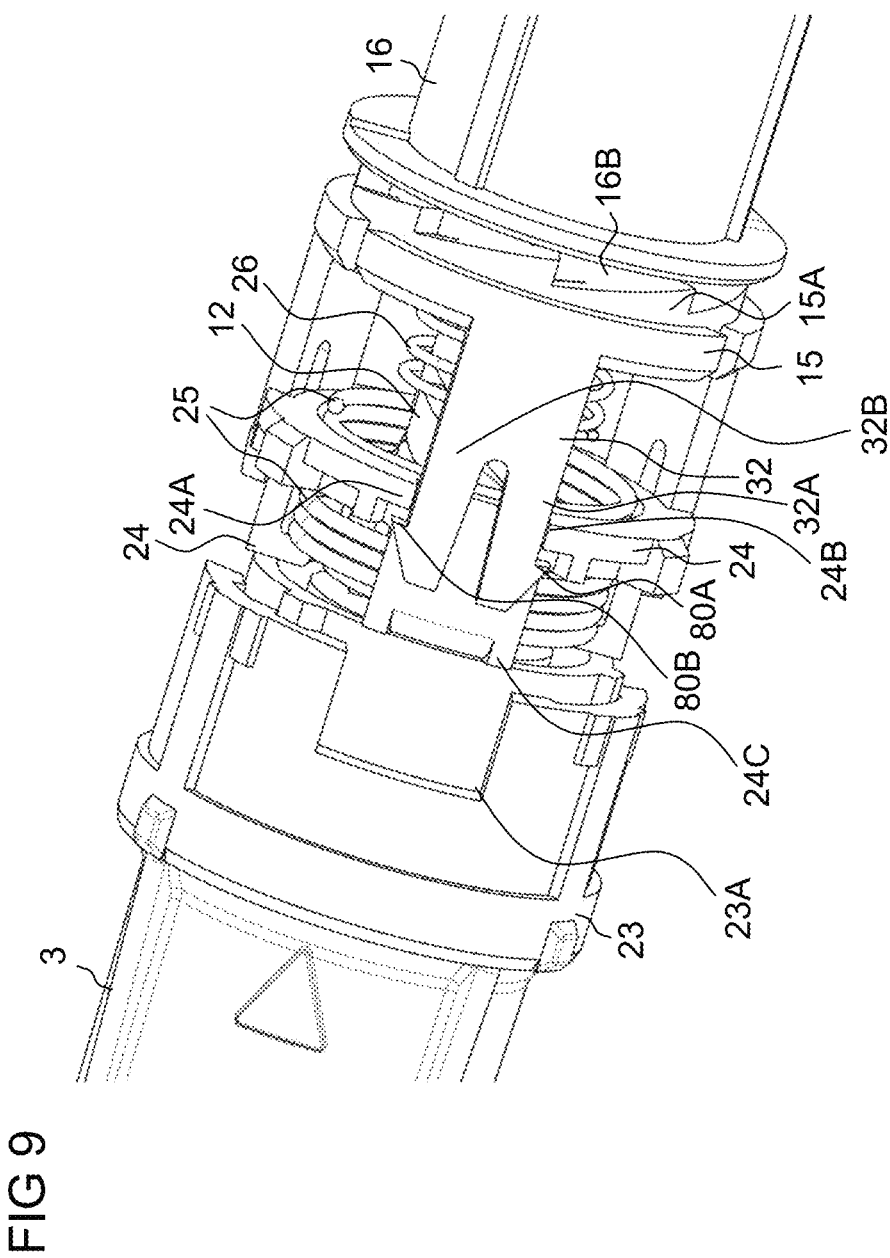
FIG. 9 shows a perspective side view of parts of the drug delivery device of FIG. 2.

According to the embodiment shown in FIG. 9, the stop member 15 is not axially securable to the housing 2 in the reset mode.

Figure 11:
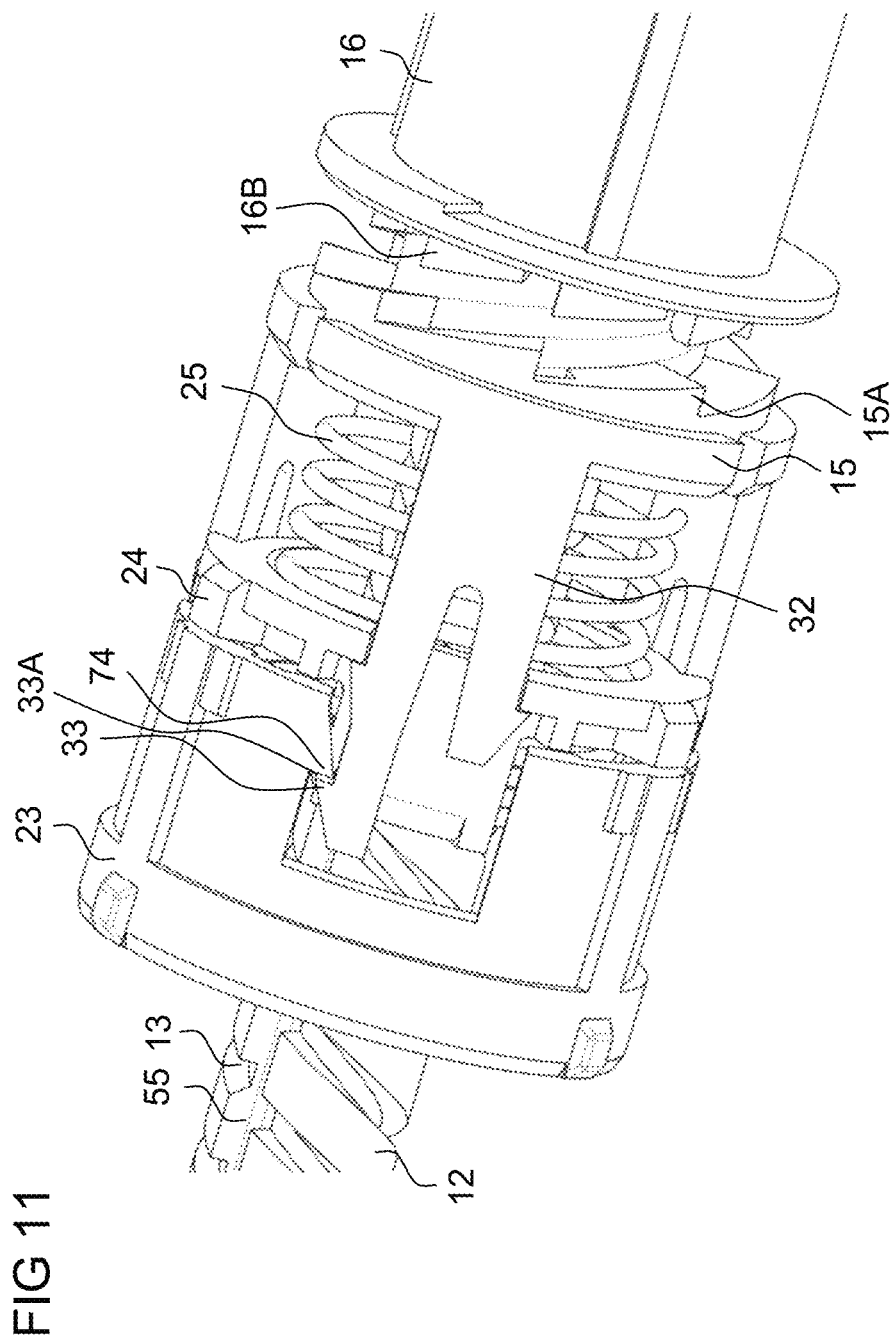
FIG. 11 shows a perspective side view of parts of the drug delivery device of FIG. 10 in the reset mode.

According to the embodiment shown in FIGS. 10 and 11, the stop member 15 is releasably securable to the housing 2 in the reset mode. The stop member 15 may be securable to the housing 2 by means of a releasable connection such that the stop member 15 is prevented from axial, in particular proximal movement with respect to the housing 2 when the device 1 is switched from the reset mode into the operational mode which is described later on in more detail.

According to this embodiment, the stop member 15 may comprise an additional engaging member 33. Engaging member 33 may be resilient. The housing 2 may comprise a mating engaging member 74. Mating engaging member 74 may be arranged on the securing member 23, for example. The engaging member 33 may be adapted and arranged to mechanically cooperate with, in particular to engage with, mating engaging member 74 such that the stop member 15 is releasably secured to the housing 2, e.g. by a snap-fit connection, in particular when the device 1 is switched from the reset mode back into the operational mode.

Engaging member 33 may comprise a ramp-like feature having a steep edge 33A (see FIGS. 10 and 11). Engaging member 33 may be provided on the interaction element 32. Engaging member 33 may be provided in the distal section of the interaction element 32, for example in the distal section of leg 32B. According to this embodiment, leg 32B may extend further in the distal direction than leg 32A. Leg 32B may be received by the securing member 23, in particular the receiving member 23A in the reset mode. Interaction element 74 may comprise a ramp-like structure. The ramp may have a steep edge which runs transversally with respect to the rotation axis.

When the stop member 15 is moved distally when the device 1 is switched into the reset mode, the engaging member 33 may be flexed, in particular by the ramp of engaging member 33 sliding along the ramp of engaging member 74. When the reset member 24 has reached the reset position, the engaging member 33 may relax and snap over the edge of mating engaging member 74. The steep edge 33A of the engaging member 33 may travel past engaging member 74 due to the distally directed force exerted onto the stop member 15 by means of the resilient reset member 25. Said force may keep the engaging member 74 and the steep edge 33A at a small distance from one another when the device 1 is in the reset mode. If the force exerted by the resilient reset member 25 is not great enough to maintain the small gap between the engaging member 74 and the engaging member 33, said members may abut when the device 1 is in the reset mode. The small gap between the engaging member 74 and the engaging member 33 may help to prevent a permanent mechanical load acting on the engaging members 33 and 74 when the device 1 is in the reset mode.

The force exerted by the resilient reset member 25 onto the stop member 15 may prevent the stop member 15 from moving proximally with respect to the housing 2 when the device 1 is in the reset mode. Further distal movement of the stop member 15 is prevented by means of the reset member 24 abutting the securing member 23.

When the reset member 24 is in the reset position, the drive member 16, the stop member 15 and the rotation member 17 may be completely disengaged from one another (see FIGS. 4A, 4B, 5A and 5B). Now, a replacement cartridge holding at least one, preferably a plurality, of doses of the drug 35 may be introduced into the cartridge holder 3 which is described below in detail. The piston rod 12 may be moveable in the proximal direction with respect to the housing 2 towards the proximal starting position (see FIGS. 8A and 8B). Thereby, the drive member 16 is rotated in the first rotational direction with respect to the stop member 15 and to the rotation member 17.

The cartridge holder 3 holding the replacement cartridge may be secured to the housing 2 again. Alternatively, the replacement cartridge may be secured directly to the housing 2. When the replacement cartridge or when the cartridge holder 3 holding the replacement cartridge are attached to the device 1 the replacement cartridge and/or cartridge holder 3 are configured to cooperate with the reset member 24 which is described below in detail. Due to mechanical cooperation of the cartridge holder 3 or the replacement cartridge and the reset member 24, the device 1 may be switched from the reset mode back into the operational mode for dispensing the drug held in the replacement cartridge.

For securing the replacement cartridge or the cartridge holder 3 to the housing 2, the replacement cartridge and/or the cartridge holder 3 may be moved proximally with respect to the housing 2, movement of the cartridge or the cartridge holder 3 thereby being guided by the first section 36A, in particular by mechanical cooperation of the first section 36A and the guide feature of the cartridge or the cartridge holder 3. Accordingly, rotation of the cartridge or the cartridge holder 3 may be prevented. The bung held in the replacement cartridge is configured to mechanically cooperate with the bearing member 14 (see FIG. 1) when the replacement cartridge is moved proximally. Accordingly, when the cartridge is moved proximally, the piston rod 12 is also moved proximally and the drive member 16 is rotated in the first rotational direction.

When moving the replacement cartridge or the cartridge holder 3 proximally a proximal face of the replacement cartridge or of the cartridge holder 3 is brought into mechanical cooperation with a distal face of the reset member 24, e.g. a face of the guide member 24C. In this way, proximal movement of the cartridge or the cartridge holder 3 may be transferred into proximal movement of the reset member 24 towards the operating position. Thereby, resilient reset member 25 is biased, e.g. compressed. Thus, the force which the resilient reset member 25 exerts on the resilient operating member 26 is reduced.

According to the embodiment shown in FIG. 9, where the stop member 15 is not releasably securable to the housing 2, as the force exerted by the resilient reset member 25 is reduced, the resilient operation member 26 may exert a force on the stop member 15, thus moving the stop member 15 in the proximal direction with respect to the housing 2 while the reset member 24 is moved into the operating position. In this way, when the piston rod 12 has reached the proximal starting position, the stop member 15 is brought back into mechanical cooperation with the drive member 16 (see FIG. 7B). Furthermore, when the reset member 24 is moved proximally back towards the operating position, the resilient operating member 26 acts on the stop member 15 and the drive member 16 such that the stop member 15 and the drive member 16 are brought back into mechanical cooperation with the rotation member 17 when the piston rod 12 has reached the proximal starting position.

Thereby, the biasing member 27 is biased. When the stop member 15, the drive member 16 and the rotation member 17 are completely re-engaged, the device 1 may be back in the operational mode. The cartridge or the cartridge holder may be guideable along the second section 36B for securing the cartridge or the cartridge holder 3 to the housing 2. The device 1 may now be ready for dispensing the drug held in the replacement cartridge (see FIGS. 7A, 7B, 8A and 8B). In particular, the drive member 16 is prevented from rotation in the first rotational direction with respect to the stop member 15 and, thus, the piston rod 12 is prevented from movement in the proximal direction with respect to the housing 2 during dose setting.

According to the embodiment shown in FIGS. 10 and 11, where the stop member 15 is releasably securable to the housing 2, again proximal movement of the cartridge or the cartridge holder 3 is transferred into proximal movement of the reset member 24 towards the operating position as described above. Thereby, resilient reset member 25 is biased, e.g. compressed. Accordingly, the force exerted by the resilient reset member 25 onto the stop member 15 which may keep the engaging member 33 at the small distance from mating engaging member 74 is reduced such that engaging member 33 and mating engaging member 74 may abut. Accordingly, further proximal movement of the stop member 15 which would be necessary for re-engaging the stop member 15 and the drive member 16 may now be prevented due to the releasable connection of the stop member 15, in particular engaging member 33, and the housing 2, in particular mating engaging member 74. Said connection has to be released for moving the stop member 15 proximally. This connection operates independently from the force exerted by the reset resilient member 25 onto the stop member 15.

For this purpose, the cartridge or the cartridge holder 3 comprises an interaction member 34 (see FIG. 10). Interaction member 34 may be arranged on an outer surface of the cartridge or the cartridge holder 3. Due to mechanical cooperation of the interaction member 34 and the stop member 15, in particular engaging member 33, the releasable connection of the stop member 15 and the housing 2 may be released when the replacement cartridge or the cartridge holder 3 are connected to the housing 2 for switching the device 1 from the reset mode back into the operational mode.

In the reset mode, in particular before the cartridge or the cartridge holder 3 is secured to the housing 2, the interaction member 34 may be arranged at a distance with respect to the engaging member 33. Accordingly, in the reset mode, mechanical cooperation of the interaction member 34 and the engaging member 33 may be prevented. In particular, mechanical cooperation may be prevented unless the cartridge or the cartridge holder 3 has reached a final proximal position with respect to the housing 2. When the cartridge is in this final proximal position, the piston rod 12 has reached its proximal starting position. In particular, when movement of the replacement cartridge or the cartridge holder 3 is guided by the first section 36A, mechanical cooperation of the interaction member 34 and the stop member 15 to release the connection of stop member 15 and the housing 2 is prevented.

When the cartridge or the cartridge holder 3 has reached the proximal end of the first section 36A, the cartridge or the cartridge holder 3 is rotated with respect to the housing 2 for securing the cartridge or the cartridge holder 3 to the housing 2. When rotating the cartridge or the cartridge holder 3, movement of the cartridge or the cartridge holder 3 is guided by the second section 36B as described above.

When the cartridge or the cartridge holder is guided by the second section 36B, the interaction member 34 is moved, in particular rotated, towards the engaging member 33. Then the engaging member 33 mechanically cooperates with the interaction member 34, such that the connection of the stop member 15 to the housing 2 is completely released when the cartridge or the cartridge holder 3 has reached a final angular position with respect to the housing 2.

The stop member 15 may now be driven in the proximal direction with respect to the drive member 16 by the energy stored in the resilient operating member 26. The force which has been exerted previously onto the resilient operating member 26 by the resilient reset member 25 was already decreased to the level that allows proximal movement of the stop member 15 driven by the resilient operating member 26 as the reset member 24 was already moved most of the way back to its operating position. Thereafter, the stop member 15 is brought into mechanical cooperation with the drive member 16. In particular the clutch connection between stop member 15 and drive member 16 is re-established. The resilient operating member 26 furthermore acts on the stop member 15 and the drive member 16 such that the drive member 16 is brought back into mechanical cooperation with the rotation member 17 as described above. Accordingly, the device 1 is in the operational mode and the drive member 16 is prevented from following rotational movement of the rotation member 17 in the first rotational direction due to mechanical cooperation with the stop member 15. The device 1 is now ready for setting and dispensing a dose of the drug held in the replacement cartridge.

Securing the stop member 15 against proximal movement with respect to the housing 2 when switching the device 1 from the reset mode into the operational mode has the advantage that it can be guaranteed that there is no mechanical cooperation between the stop member 15 and the drive member 16 until the piston rod 12 has reached its proximal starting position. This advantage is particularly important, if the reset member 24 is also moved when the piston rod 12 is moved. This may be the case, for example, when the bung of the replacement cartridge is brought into contact with the piston rod 12 and the cartridge is moved proximally together with the piston rod 12 for resetting. As movement of the cartridge also causes, from a certain point onwards in the reset operation, movement of the reset member 24, the distally directed force of the resilient reset member 25 acting on the stop member 15 is reduced and it is increasingly likely that the stop member 15 would be moved proximally before the piston rod 12 has reached its proximal starting position. This movement is undesirable as a re-engagement of drive 16 member and stop member 15 before the piston 12 rod has been moved back into its proximal starting position would prevent further proximal movement of the piston rod 12 and, thus, also completion of the reset operation, because stop member 15 and drive member 16 had re-engaged too early. Re-engagement of the stop member 15 and the drive member 16 should thus be guaranteed to take place only when the piston rod 12 is in its proximal starting position. This can be achieved by securing the stop member 15 against proximal movement—expediently in the reset mode and/or until the end of the operation for switching from the reset mode into the operational mode—independently from the force exerted by the resilient reset member 25 onto the stop member 15.

The invention claimed is:

1. An assembly for a drug delivery device, comprising:
   a housing having a distal end and a proximal end,
   a rotation member adapted and arranged to be rotated in a first rotational direction and in a second rotational direction with respect to the housing in an operational mode of the assembly,
   a drive member which is configured to mechanically cooperate with the rotation member such that the drive member follows rotation of the rotation member when the rotation member is rotated in the second rotational direction and such that the rotation member rotates with respect to the drive member when the rotation member is rotated in the first rotational direction,
   a piston rod configured to engage the drive member, the piston rod being adapted and arranged to be driven in the distal direction with respect to the housing when the drive member is rotated in the second rotational direction,
   at least one biasing member which is adapted and arranged to provide a force tending to bring the rotation member and the drive member out of mechanical cooperation in the operational mode,
   wherein the assembly is switchable from the operational mode into a reset mode, and wherein, for switching from the operational mode into the reset mode, the biasing member is configured to drive a relative axial movement between the drive member and the rotation member such that the rotation member and the drive member are brought out of mechanical cooperation.

2. The assembly according to claim 1, comprising a stop member, the drive member and the stop member being coupled to one another by a uni-directional friction clutch mechanism in the operational mode such that rotation of the drive member in the first rotational direction with respect to the stop member is prevented and such that rotational movement of the drive member in the second rotational direction with respect to the stop member is permitted.

3. The assembly according to claim 2, wherein the stop member is rotationally locked to the housing in the operational mode and in the reset mode, and wherein the stop member is axially displaceable with respect to the housing.

4. The assembly according to claim 2, comprising a reset member which is adapted and arranged to be moved with respect to the housing between an operating position and a reset position, wherein, when the reset member is in the operating position, the drive member mechanically cooperates with the stop member and the rotation member, and wherein, when the reset member is in the reset position, the drive member is prevented from mechanical cooperation with the stop member and the rotation member, and wherein the drive member is rotatable in the first rotational direction with respect to the housing.

5. The assembly according to claim 4, comprising a resilient reset member, wherein, in the operational mode, the resilient reset member is configured to be biased thereby tending to move the reset member from the operating position into the reset position and, wherein, when the assembly is switched from the operational mode into the reset mode, the resilient reset member is permitted to relax, thereby moving the reset member from the operating position into the reset position.

6. The assembly according to claim 4, wherein the stop member and the reset member are configured to mechanically cooperate with one another such that the stop member follows movement of the reset member towards the reset position, thereby being brought out of mechanical cooperation with the drive member.

7. The assembly according to claim 2, comprising a resilient operating member which is adapted and arranged to exert a force onto one, two or all of the drive member, the stop member and the rotation member, which force keeps the drive member in permanent mechanical cooperation with the stop member and the rotation member in the operational mode.

8. The assembly according to claim 5, comprising a resilient operating member which is adapted and arranged to exert a force onto one, two or all of the drive member, the stop member and the rotation member, which force keeps the drive member in permanent mechanical cooperation with the stop member and the rotation member in the operational mode, wherein the resilient reset member is a reset spring member, the biasing member is a biasing spring member and the resilient operating member is an operating spring member, wherein the spring strength of the reset spring member is greater than the spring strength of the operating spring member and, wherein the spring strength of the operating spring member is greater than the spring strength of the biasing spring member.

9. The assembly according to claim 8, wherein the spring strength of the biasing spring member is great enough to achieve a relative movement between the rotation member and the drive member to bring said members out of mechanical cooperation.

10. The assembly according to claim 1, wherein the drive member and the piston rod are rotationally locked with each other.

11. The assembly according to claim 4, wherein, in the reset mode, the stop member is secured to the housing by means of a releasable connection such that the stop member is prevented from axial movement in the proximal direction with respect to the reset member and with respect to the drive member.

12. The assembly according to claim 5, comprising a trigger member releasably connectable to the housing, wherein, when the trigger member is connected to the housing, the trigger member is arranged to prevent the resilient reset member from relaxing, and wherein, when the trigger member is disconnected from the housing the assembly is switched from the operational mode into the reset mode.

13. The assembly according to claim 11, wherein the housing comprises a guide track which is adapted and arranged to mechanically cooperate with a trigger member to guide movement of the trigger member with respect to the housing when the trigger member is connected to or disconnected from the housing, the guide track comprising a first section and a second section, the proximal end of the first section defining a proximal end position for the trigger member with respect to the housing and the second section extending in an angular direction, wherein, when movement of the trigger member is guided by the first section in the reset mode, mechanical cooperation between the stop member and the trigger member is prevented, and wherein, when movement of the trigger member is guided by the second section in the reset mode, the trigger member and the stop member are permitted to mechanically cooperate to release the connection of the stop member to the housing for switching the assembly into the operational mode such that the stop member is arranged to prevent rotation of the drive member in the first rotational direction, thereby preventing movement of the piston rod with respect to the housing during dose setting.

14. The assembly according to claim 7, wherein, when the assembly is in the reset mode, energy is stored in the resilient operating member to drive movement of the stop member to switch the assembly into the operational mode.

15. A drug delivery device comprising the assembly according to claim 1 and a cartridge, the cartridge holding a plurality of doses of a drug, wherein the drug delivery device is a pen-type fixed dose device.

16. An assembly for a drug delivery device, comprising:
a housing having a distal end and a proximal end,
a rotation member adapted and arranged to be rotated in a first rotational direction and in a second rotational direction with respect to the housing in an operational mode of the assembly,
a drive member which is configured to mechanically cooperate with the rotation member such that the drive member follows rotation of the rotation member when the rotation member is rotated in the second rotational direction and such that the rotation member rotates with respect to the drive member when the rotation member is rotated in the first rotational direction,
a piston rod adapted and arranged to be driven in the distal direction with respect to the housing when the drive member is rotated in the second rotational direction,
at least one biasing member which is adapted and arranged to provide a force tending to bring the rotation member and the drive member out of mechanical cooperation in the operational mode,
wherein the assembly is switchable from the operational mode into a reset mode, and wherein, for switching from the operational mode into the reset mode, the biasing member is configured to drive a relative axial movement between the drive member and the rotation member such that the rotation member and the drive member are brought out of mechanical cooperation,
the assembly further comprising a stop member, the drive member and the stop member being coupled to one another by a uni-directional friction clutch mechanism in the operational mode such that rotation of the drive member in the first rotational direction with respect to the stop member is prevented and such that rotational movement of the drive member in the second rotational direction with respect to the stop member is permitted,
further comprising a reset member which is adapted and arranged to be moved with respect to the housing between an operating position and a reset position, wherein, when the reset member is in the operating position, the drive member mechanically cooperates with the stop member and the rotation member, and wherein, when the reset member is in the reset position, the drive member is prevented from mechanical cooperation with the stop member and the rotation member, and wherein the drive member is rotatable in the first rotational direction with respect to the housing, and
further comprising a resilient reset member, wherein, in the operational mode, the resilient reset member is configured to be biased thereby tending to move the reset member from the operating position into the reset position and, wherein, when the assembly is switched from the operational mode into the reset mode, the resilient reset member is permitted to relax, thereby moving the reset member from the operating position into the reset position, and
wherein the resilient reset member is a reset spring member, the biasing member is a biasing spring member and the resilient operating member is an operating spring member, wherein the spring strength of the reset spring member is greater than the spring strength of the operating spring member, and wherein the spring strength of the operating spring member is greater than the spring strength of the biasing spring member.

* * * * *